(12) United States Patent
Blaszczak et al.

(10) Patent No.: US 8,106,090 B2
(45) Date of Patent: Jan. 31, 2012

(54) 1-AMINO LINKED COMPOUNDS

(75) Inventors: Larry Chris Blaszczak, Indianapolis, IN (US); Shon Roland Pulley, Noblesville, IN (US); Michael Alan Robertson, Indianapolis, IN (US); Scott Martin Sheehan, Carmel, IN (US); Qing Shi, Carmel, IN (US); Michael Robert Wiley, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 952 days.

(21) Appl. No.: 11/996,128

(22) PCT Filed: Jul. 14, 2006

(86) PCT No.: PCT/US2006/027671
§ 371 (c)(1),
(2), (4) Date: Jan. 18, 2008

(87) PCT Pub. No.: WO2007/015805
PCT Pub. Date: Feb. 8, 2007

(65) Prior Publication Data
US 2008/0207735 A1 Aug. 28, 2008

Related U.S. Application Data

(60) Provisional application No. 60/700,872, filed on Jul. 20, 2005.

(51) Int. Cl.
*C07D 207/04* (2006.01)
*A61K 31/40* (2006.01)

(52) U.S. Cl. ..... 514/428; 514/287; 514/406; 548/304.4; 548/361.1; 548/569

(58) Field of Classification Search ........................ None
See application file for complete search history.

(56) References Cited

U.S. PATENT DOCUMENTS

| 5,968,942 | A | 10/1999 | Vazquez et al. |
| 2004/0167133 | A1 | 8/2004 | Edmondson et al. |
| 2004/0236102 | A1 | 11/2004 | Brockunier et al. |

FOREIGN PATENT DOCUMENTS

| EP | 346827 A2 | 12/1989 |
| EP | 361341 A2 | 4/1990 |
| EP | 560268 A1 * | 9/1993 |
| EP | 604185 A1 | 6/1994 |
| WO | WO 94/04492 A | 3/1994 |
| WO | WO 95/09843 A1 | 4/1995 |
| WO | WO 95/21164 A1 | 8/1995 |
| WO | WO 96/28465 A1 | 9/1996 |
| WO | WO 99/29311 A | 6/1999 |
| WO | WO 02/02512 A2 | 1/2002 |
| WO | WO 03/000180 A2 | 1/2003 |
| WO | WO 03/000181 A2 | 1/2003 |
| WO | WO 03/004498 A1 | 1/2003 |
| WO | WO 03/082817 A2 | 10/2003 |
| WO | WO 2004/037169 A2 | 5/2004 |
| WO | WO 2007/015767 | 2/2007 |
| WO | WO 2007/015807 | 2/2007 |

OTHER PUBLICATIONS

Beaulieu P L et al, "Practical, Stereoselective Synthesis of Palinavir, a Potent HIV Protease Inhibitor", Journal of Organic Chemistry, American Chemical Society. Easton, US, vol. 62, No. 11, 1997, pp. 3440-3448, XP002304500.
Howard, Nigel et al., "Application of Fragment Screening and Fragment Linking to the Discovery of Novel Thrombin Inhibitors", Journal of Medicinal Chemistry, 49(4), 1346-1355 Coden: JMCMAR; ISNN: 0022-2623, 2006, XP002406118. C. Rummey et al, "In silico fragment-based discovery of DPP-IV S1 pocket binders", Bioorganic & Medicinal Chemistry Letters 16 (2006), pp. 1405-1409.
J. Peters et al, "Aminomethylpyrimidines as novel DPP-IV inhibitors: A $10^5$-fold activity increase by optimization of aromatic substituents", Bioorganic & Medicinal Chemistry Letters 14 (2004), pp. 1491-1493.

* cited by examiner

*Primary Examiner* — Zinna Northington Davis
(74) *Attorney, Agent, or Firm* — James B. Myers

(57) ABSTRACT

The present invention is directed to compounds of formula (I): or a pharmaceutically acceptable salt thereof; wherein A is (II); X is selected from CH, CF and N, R8 is selected from H, $C_1$-$C_6$ alkyl, aryl, heteroaryl, $C_1$-$C_6$ alkylaryl, $C_1$-$C_6$ alkylheteroaryl, $C_2$-$C_6$ alkyl-O—$C_1$-$C_6$ alkyl, $C_1$-$C_6$ haloalkyl, hydroxy $C_2$-$C_6$ alkyl, —C(O)R9 and —SO$_2$R9, or R7 and R8 combine to form (III), (IV); W is selected from CR1O and CR15, R1O is selected from H, halo, —C(O)NR13R14, $C_1$-$C_6$ alkyl, aryl, heteroaryl, $C_1$-$C_6$ alkylaryl, $C_1$-$C_6$ alkylheteroaryl, $C_1$-$C_6$ alkyl-O—$C_1$-$C_6$ alkyl and hydroxy $C_1$-$C_6$ alkyl; Het is a N-linked 5-membered heteroaryl ring optionally substituted with 1-3 substituents selected from methoxy, Cl, F, $CH_3$, $CF_3$, aryl, heteroaryl, $C_1$-$C_4$ alkylaryl or $C_1$-$C_4$ alkylheteroaryl, for use as inhibitors of the DPP-IV enzyme in the treatment or prevention of conditions including Type II diabetes.

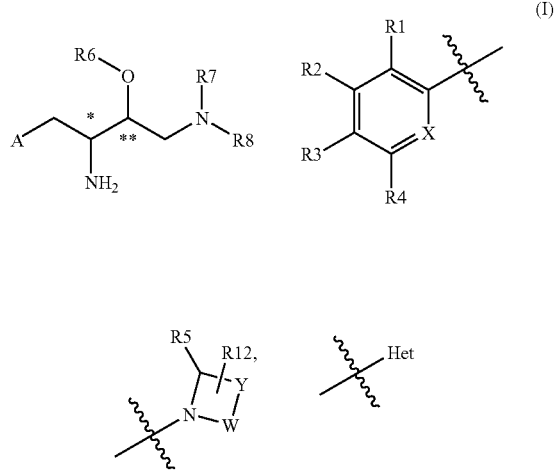

27 Claims, No Drawings

1-AMINO LINKED COMPOUNDS

REFERENCE TO RELATED APPLICATION

This application is submitted as a United States national phase entry, pursuant to 35 U.S.C. §371, of PCT/US2006/027671, filed on 14 Jul. 2006, which claims the benefit of U.S. provisional patent application Ser. No. 60/700,872, filed 20 Jul. 2005, each of which is incorporated by reference herein.

BACKGROUND OF THE INVENTION

Diabetes is a chronic disease that features abnormal glucose homeostasis, the disease has been differentiated into two forms; Type I or insulin-dependent diabetes mellitus (IDDM) and Type II or non-insulin-dependent diabetes mellitus (NIDDM). Type II diabetes accounts for 90% of all cases of diabetes and in 1994 was estimated by the World Health Organization to affect 2-3% of the world's population with diagnosis rates rising at 4-5% per year.

The initial stage of Type II diabetes is characterized by insulin resistance which is initially compensated, in part, by increased production of insulin by pancreatic β cells, over time these cells become exhausted and insulin production decreases. The combined effects of insulin resistance and decreased insulin production reduce glucose uptake and utilization by skeletal muscle and prevent insulin-mediated suppression of hepatic glucose output. As the disease progresses blood glucose levels increase, postprandial hyperglycaemia is observed which upon further development leads to a state of fasting hyperglycaemia.

Type II diabetes is a component of a disease cluster known as metabolic syndrome, comprising a variety of disorders including glucose intolerance/insulin resistance, arterial hypertension, dyslipidaemia and obesity. For Type II diabetic patients suffering from poor glycaemic control the major cause for concern are chronic complications such as retinopathy, nephropathy, neuropathy and atherosclerosis.

The treatments currently available for Type II diabetes range from increased exercise in combination with decreased calorific intake to, when other treatment options fail, the injection of exogenous insulin. Within this range of treatments are a number of oral pharmacological agents which may be administered individually or, for patients where the disease is more advanced, in combination to achieve better glycaemic control.

Current oral pharmacological agents include sulfonylureas (e.g. tolbutamide) and glinides which stimulate the pancreatic β cells, increasing insulin secretion. Also, acarbose which is an α-glucosidase inhibitor that reduces the rate of intestinal carbohydrate digestion and therefore absorption. Biguanidines, such as metformin and glitazones, counter insulin resistance by decreasing hepatic glucose output and increasing muscle insulin sensitivity. The glitazones (thiazolidinediones) exert their action by acting as agonists of the peroxisome proliferator activated receptor (PPAR) and more particularly the PPAR-γ receptor.

As a consequence of side effects associated with the current oral pharmacological agents, namely, sulfonylurea and glinide induced hypoglycaemia, acarbose induced gastrointestinal disturbances, metformin induced lactic acidosis and glitazone induced liver toxicity, there continues to be a demand for the development of alternative oral antidiabetic agents.

There are a wide variety of alternative approaches to glycaemic control currently under investigation. Alternative approaches under investigation include, treatment with PPAR-α or PPAR-δ agonists, rexinoid X receptor (RXR) agonists, protein tyrosine phosphotase 1B (PTP-1B) inhibitors and glycogen synthase kinase (GSK)-3 inhibitors.

Dipeptidyl peptidase IV (DPP-IV) is a widely expressed glycoprotein present in cells in most tissues, including the kidney, gastrointestinal tract and liver and is responsible for the rapid degradation of several regulatory peptides including the incretin hormones, glucagon-like peptide-1 (GLP-1) and glucose-dependent insulinotropic polypeptide (GIP). GLP-1 is released from the intestinal tract wall into the bloodstream in response to nutrient ingestion and is an integral component in the physiological control of insulin release, and therefore the regulation of blood glucose. Inhibiting DPP-IV enhances the body's normal homeostatic mechanisms resulting in increased levels of GLP-1, lead to higher plasma insulin concentrations and thus regulate blood glucose.

Advantageously, DPP-IV inhibitors in utilising the body's normal homeostatic mechanisms, insulin levels will only be increased at appropriate times such as in response to nutrient ingestion. This mode of action significantly reduces the risk of hypoglycaemia, and highlights DPP-IV inhibitors as a target of interest for the development of alternative oral antidiabetic agents.

Compounds that are inhibitors of DPP-IV and which may be useful in the treatment of diabetes have been described in the art. These compounds include thiazolidine derivatives (e.g. *Drugs of the Future*, (2001) 26: 859-864, WO 99/61431, U.S. Pat. No. 6,110,949, WO 03/037327) and pyrrolidine derivatives (e.g. *Diabetes*, (2002) 51: 1461-1469, WO 98/19998, WO 01/40180, WO 03/037327). Other compounds include piperidine, piperizine and morpholine derivatives (e.g. WO 03/000181, WO 03/082817). Still others include pyridine derivatives (e.g. WO 03/068748, WO 03/068757, WO 05/042488)

The present invention relates to 1-amino linked compounds which are inhibitors of the DPP-IV enzyme, pharmaceutical compositions containing them as active ingredient, methods for the treatment or prevention of diseases in which the DPP-IV enzyme is involved, to their use as medicaments and to their use in the manufacture of medicaments for the treatment or prevention of diseases in which the DPP-IV enzyme is involved, such as diabetes and particularly Type II diabetes.

The compounds of the present invention are described by structural formula I:

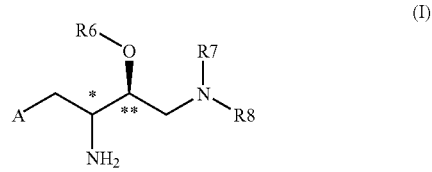

or a pharmaceutically acceptable salt thereof;
wherein
A is

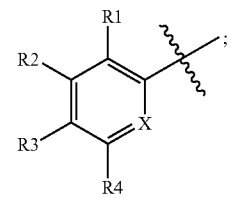

R1 is selected from H, halo, $C_1$-$C_4$ alkyl, $C_1$-$C_4$ alkoxy, $C_1$-$C_4$ haloalkyl, $C_1$-$C_4$ haloalkoxy, CN and hydroxy;

R2, R3, and R4 are independently selected from H, halo, methyl, ethyl, methoxy, $C_1$-$C_2$ haloalkyl, $C_1$ haloalkoxy, CN and hydroxy;

X is selected from CH, CF and N;

R6 is independently selected from H, $C_1$-$C_6$ alkyl and $C_3$-$C_6$ cycloalkyl;

R7 is selected from H, $C_1$-$C_6$ alkyl, aryl, heteroaryl, $C_1$-$C_6$ alkylaryl, $C_1$-$C_6$ alkylheteroaryl, $C_2$-$C_6$ alkyl-O—$C_1$-$C_6$ alkyl, $C_1$-$C_6$ haloalkyl and hydroxy $C_2$-$C_6$ alkyl;

R8 is selected from H, $C_1$-$C_6$ alkyl, aryl, heteroaryl, $C_1$-$C_6$ alkylaryl, $C_1$-$C_6$ alkylheteroaryl, $C_2$-$C_6$ alkyl-O—$C_1$-$C_6$ alkyl, $C_1$-$C_6$ haloalkyl, hydroxy $C_2$-$C_6$ alkyl, —C(O)R9 and —SO$_2$R9, or R7 and R8 combine to form

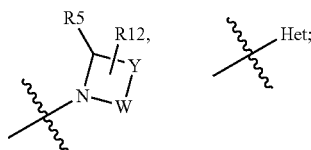

R9 is selected from $C_1$-$C_6$ alkyl, $C_1$-$C_6$ haloalkyl, aryl, heteroaryl, $C_1$-$C_6$ alkylaryl and $C_1$-$C_6$ alkylheteroaryl;

R5 is selected from H, halo, $C_1$-$C_6$ alkyl, aryl, heteroaryl, $C_1$-$C_6$ alkylaryl, $C_1$-$C_6$ alkylheteroaryl, $C_1$-$C_6$ alkyl-O—$C_1$-$C_6$ alkyl and hydroxy $C_1$-$C_6$ alkyl;

Y is selected from —CH$_2$—Y'—, —CH$_2$—CH$_2$—Y'—, —Y'—CH$_2$—, —Y'—CH$_2$—CH$_2$— and —CH$_2$—Y"—CH$_2$—;

Y' is selected from CR11, CR15 and S;

Y" is selected from CR11, CR15, NR16, N—CH$_3$, CHF, CF$_2$, O and S;

W is selected from CR10 and CR15

R10 is selected from H, halo, —C(O)NR13R14, $C_1$-$C_6$ alkyl, aryl, heteroaryl, $C_1$-$C_6$ alkylaryl, $C_1$-$C_6$ alkylheteroaryl, $C_1$-$C_6$ alkyl-O—$C_1$-$C_6$ alkyl and hydroxy $C_1$-$C_6$ alkyl;

R11 and R12 are independently selected from H, halo, $C_1$-$C_6$ alkyl, aryl, heteroaryl, $C_1$-$C_6$ alkylaryl, $C_1$-$C_6$ alkylheteroaryl, $C_1$-$C_6$ alkoxy, $C_1$-$C_6$ alkyl-O—$C_1$-$C_6$ alkyl, $C_1$-$C_6$ haloalkyl, $C_1$-$C_6$ haloalkoxy, hydroxy $C_1$-$C_6$ alkyl, CN and hydroxy;

R13 and R14 are independently selected from H, $C_1$-$C_6$ alkyl, $C_1$-$C_6$ haloalkyl, aryl, heteroaryl, $C_1$-$C_6$ alkylaryl and $C_1$-$C_6$ alkylheteroaryl or R13 and R14 combine with the N of —C(O)NR13R14 to form a 4 to 8 membered heterocyle;

R15 combines with R11 or R12 to form a phenyl or 5-6 membered heteroaryl ring optionally substituted with 1-3 substituents selected from methoxy, Cl, F, CH$_3$ and CF$_3$;

R16 combines with R11 or R12 to form a 5-6 membered heteroaryl ring optionally substituted with 1-3 substituents selected from methoxy, Cl, F, CH$_3$ and CF$_3$;

where R7, R8, R9, R10, R11, R12, R13 or R14 are aryl, heteroaryl, $C_1$-$C_6$ alkylaryl or $C_1$-$C_6$ alkylheteroaryl the aryl or heteroaryl substituents are optionally substituted with 1-3 substituents selected from methoxy, Cl, F, CH$_3$ and CF$_3$;

Het is a N-linked 5-membered heteroaryl ring optionally substituted with 1-3 substituents selected from methoxy, Cl, F, CH$_3$, CF$_3$, aryl, heteroaryl, $C_1$-$C_4$ alkylaryl or $C_1$-$C_4$ alkylheteroaryl, or a N-linked 5-membered heteroaryl ring fused with phenyl or a 5-6 membered heteroaryl ring optionally substituted with 1-3 substituents selected from methoxy, Cl, F, CH$_3$ and CF$_3$;

with the proviso that where R7 and R8 combine to form

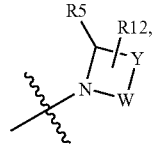

Y is —CH$_2$—Y'— or —Y'—CH$_2$—, Y' is CR11, W is CR10, R10 is —C(O)NR13R14, X is CH, R1 is H, R2 is H, R3 is H, R4 is H, R5 is H, R6 is H, R1 is H, R12 is H, R13 is H and R14 is H or t-butyl, then at the C atom designated as * the bond to the NH$_2$ substituent must be designated as ⋯⋯;

with the further proviso that a compound of formula I is not (2S)-1-([2R,3S]-3-Amino-2-hydroxy-4-phenyl-butyl)-pyrrolidine-4-hydroxy-2-carboxylic acid tert-butylamide or 1-(3-Amino-2-hydroxy-4-phenyl-butyl)-pyrrolidine-2-carboxylic acid (2-pyridin-2-yl-ethyl)-amide.

A preferred species of the compounds of formula I are compounds of formula II:

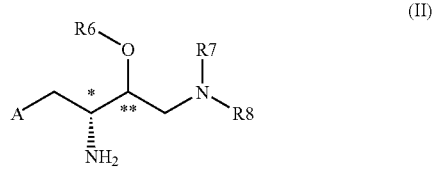

or a pharmaceutically acceptable salt thereof wherein A, R6, R7 and R8 are as defined herein.

A preferred species of the compounds of formula I are compounds of formula III:

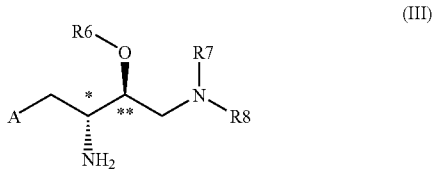

or a pharmaceutically acceptable salt thereof wherein A, R6, R7 and R8 are as defined herein.

A preferred species of the compounds of formula I are compounds of formula Ia:

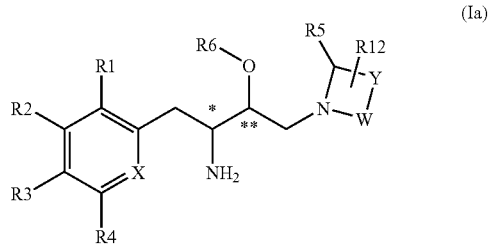

or a pharmaceutically acceptable salt thereof wherein X, Y, W, R1, R2, R3, R4, R5, R6 and R12 are as defined herein.

A preferred species of the compounds of formula I are compounds of formula Ib:

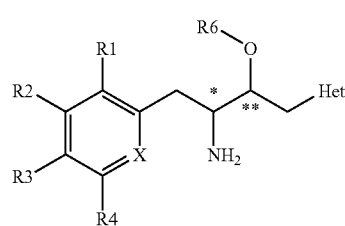

(Ib)

or a pharmaceutically acceptable salt thereof wherein Het, R1, R2, R3, R4 and R6 are as defined herein.

A preferred species of the compounds of formula II are compounds of formula IIa:

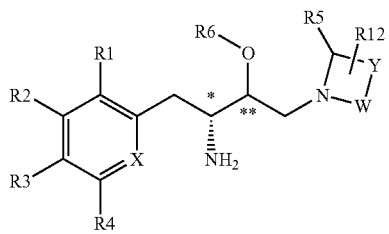

(IIa)

or a pharmaceutically acceptable salt thereof wherein X, Y, W, R1, R2, R3, R4, R5, R6 and R12 are as defined herein.

A preferred species of the compounds of formula II are compounds of formula IIb:

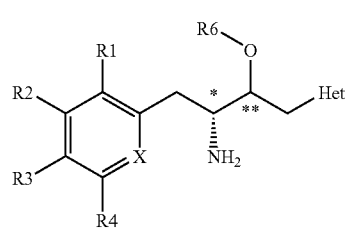

(IIb)

or a pharmaceutically acceptable salt thereof wherein Het, R1, R2, R3, R4 and R6 are as defined herein.

A preferred species of the compounds of formula III are compounds of formula IIIa:

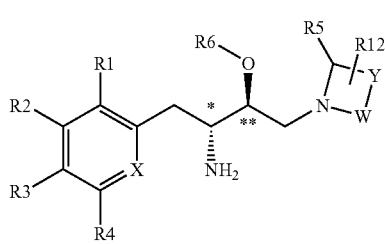

(IIIa)

or a pharmaceutically acceptable salt thereof wherein X, Y, W, R1, R2, R3, R4, R5, R6 and R12 are as defined herein.

A preferred species of the compounds of formula III are compounds of formula IIIb:

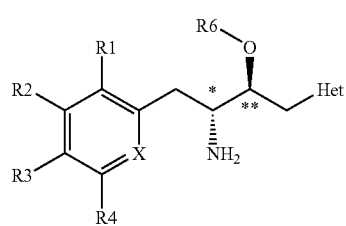

(IIIb)

or a pharmaceutically acceptable salt thereof wherein Het, R1, R2, R3, R4 and R6 are as defined herein.

A preferred species of the compounds of formula Ia are compounds of formula Ia(i):

(Ia(i))

or a pharmaceutically acceptable salt thereof wherein X, R1, R2, R3, R4, R5, R6, R1, R12, R13 and R14 are as defined herein.

A preferred species of the compounds of formula IIa are compounds of formula IIa(i):

(IIa(i))

or a pharmaceutically acceptable salt thereof wherein X, R1, R2, R3, R4, R5, R6, R11, R12, R13 and R14 are as defined herein.

A preferred species of the compounds of formula IIIa are compounds of formula IIIa(i):

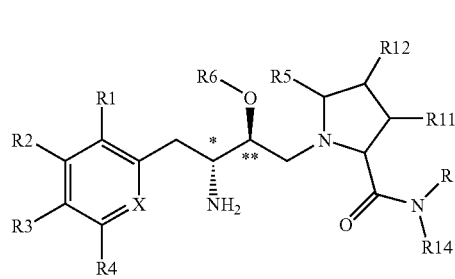

(IIIa(i))

or a pharmaceutically acceptable salt thereof wherein X, R1, R2, R3, R4, R5, R6, R11, R12, R13 and R14 are as defined herein.

A preferred species of the compounds of formula Ia(i) are compounds of formula Ia(ii):

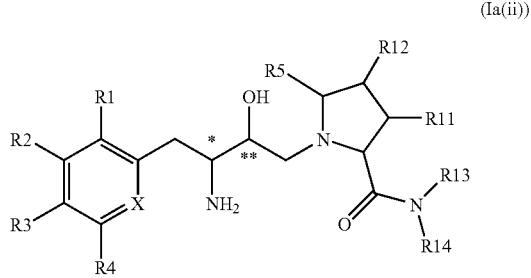

or a pharmaceutically acceptable salt thereof wherein X, R1, R2, R3, R4, R5, R11, R12 R13 and R14 are as defined herein.

A preferred species of the compounds of formula IIa(i) are compounds of formula IIa(ii):

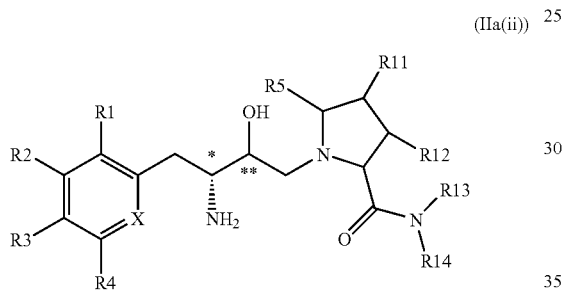

or a pharmaceutically acceptable salt thereof wherein X, R1, R2, R3, R4, R5, R11, R12, R13 and R14 are as defined herein.

A preferred species of the compounds of formula IIIa(i) are compounds of formula IIIa(ii):

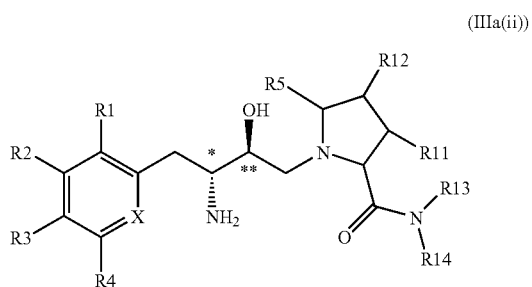

or a pharmaceutically acceptable salt thereof wherein X, R1, R2, R3, R4, R5, R11, R12, R13 and R14 are as defined herein.

In the present invention it is preferred that R1 and R4 are independently selected from H, F, Cl, $CH_3$ and $CF_3$, it is more preferred that R1 and R4 are independently selected from F, $C_1$ and $CH_3$, more preferably R1 and R4 are independently selected from F and Cl, most preferably R1 is F and R4 is either Cl or F.

In the present invention it is preferred that R2 and R3 are independently selected from H, F, Cl, $CH_3$ and $CF_3$, it is more preferred that R2 and R3 are independently selected from H, F and Cl, more preferably R2 and R3 are independently selected from H and F, most preferably R2 is H and R3 is F.

In the present invention it is preferred that where X is N, R1 is selected from H, F and $CH_3$.

In the present invention it is preferred that X is selected from CH and CF, most preferably X is CH.

In the present invention it is preferred that R5 is selected from H, F, Cl, $CH_3$ and $OCH_3$, most preferably R5 is H.

In the present invention it is preferred that R6 is selected from $CH_3$ and H, most preferably R6 is H.

In the present invention it is preferred that R7 is selected from H, $C_1$-$C_4$ alkyl and $C_1$-$C_4$ alkylaryl, more preferably R7 is selected from H, methyl, ethyl, propyl, isopropyl benzyl, phenylethyl and phenylpropyl, more preferably R7 is selected from H methyl, ethyl and isopropyl, more preferably R7 is H or methyl.

In the present invention it is preferred that R8 is selected from H, $C_1$-$C_4$ alkyl, $C_1$-$C_4$ alkylaryl and —C(O)R9, more preferably R8 is selected from H, methyl, ethyl, propyl, isopropyl benzyl, phenylethyl, phenylpropyl and —C(O)R9, more preferably R8 is selected from methyl, phenylethyl, phenylpropyl and —C(O)R9, more preferably R8 is —C(O)R9, most preferably R7 and R8 combine to form

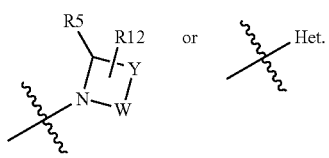

In the present invention it is preferred that R9 is selected from $C_1$-$C_4$ alkyl, aryl and $C_1$-$C_4$ alkylaryl, more preferably R9 is selected from methyl, ethyl, propyl, isopropyl, phenyl, benzyl, phenylethyl and phenylpropyl, more preferably R9 is selected from methyl, phenylethyl and phenylpropyl, most preferably R9 is methyl.

Where in the present invention R7 and R8 combine to form a substituent it is preferred that R7 and R8 combine to form

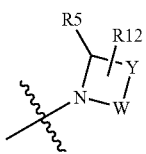

where W, Y and R12 are as defined herein.

In the present invention it is preferred that Y is selected from —$CH_2$—Y'— where Y' is CR11 and R11 is selected from H, F, Cl, $CH_3$ and $OCH_3$, most preferably R11 is H.

In the present invention it is preferred that Y is selected from —$CH_2$—$CH_2$—Y'— where Y' is CR11 and R1 is selected from H, F, Cl, $CH_3$ and $OCH_3$, most preferably R11 is H.

In the present invention it is preferred that Y is selected from —Y'—$CH_2$— where Y' is CR11 and R11 is selected from H, F, Cl, $CH_3$ and $OCH_3$, most preferably R11 is H.

In the present invention it is preferred that Y is selected from —Y'—$CH_2$—$CH_2$— where Y' is CR11 and R11 is selected from H, F, Cl, $CH_3$ and $OCH_3$, most preferably R11 is H.

In the present invention it is preferred that Y is selected from —$CH_2$—Y"—$CH_2$— where Y" is CR11 and R11 is selected from H, F, Cl, $CH_3$ and $OCH_3$, most preferably R11 is H.

In the present invention it is preferred that Y is selected from —CH₂—Y'— where Y' is CR15 and R15 combines with R11 or R12 to form a phenyl, pyridyl, pyrimidyl, pyrrolyl, pyrazolyl, isoxazolyl, isothiazolyl, imidazolyl, oxazolyl, thiazolyl or triazolyl substituent optionally substituted with 1-3 substituents selected from methoxy, Cl, F, CH₃ and CF₃; preferably R15 combines with R11 or R12 to form a phenyl, pyrrolyl, pyrazolyl or imidazolyl substituent optionally substituted with 1-3 substituents selected from methoxy, Cl, F, CH₃ and CF₃; most preferably R15 combines with R11 or R12 to form a phenyl substituent optionally substituted with 1-3 substituents selected from methoxy, Cl, F, CH₃ and CF₃.

In the present invention it is preferred that Y is selected from —CH₂—CH₂—Y'— where Y' is CR15 and R15 combines with R11 or R12 to form a phenyl, pyridyl, pyrimidyl, pyrrolyl, pyrazolyl, isoxazolyl, isothiazolyl, imidazolyl, oxazolyl, thiazolyl or triazolyl substituent optionally substituted with 1-3 substituents selected from methoxy, Cl, F, CH₃ and CF₃; preferably R15 combines with R11 or R12 to form a phenyl, pyrrolyl, pyrazolyl or imidazolyl substituent optionally substituted with 1-3 substituents selected from methoxy, Cl, F, CH₃ and CF₃; most preferably R15 combines with R11 or R12 to form a phenyl substituent optionally substituted with 1-3 substituents selected from methoxy, Cl, F, CH₃ and CF₃.

In the present invention it is preferred that Y is selected from —Y'—CH₂— where Y' is CR15 and R15 combines with R11 or R12 to form a phenyl, pyridyl, pyrimidyl, pyrrolyl, pyrazolyl, isoxazolyl, isothiazolyl, imidazolyl, oxazolyl, thiazolyl or triazolyl substituent optionally substituted with 1-3 substituents selected from methoxy, Cl, F, CH₃ and CF₃; preferably R15 combines with R11 or R12 to form a phenyl, pyrrolyl, pyrazolyl or imidazolyl substituent optionally substituted with 1-3 substituents selected from methoxy, Cl, F, CH₃ and CF₃; most preferably R15 combines with R11 or R12 to form a phenyl substituent optionally substituted with 1-3 substituents selected from methoxy, Cl, F, CH₃ and CF₃.

In the present invention it is preferred that Y is selected from —Y'—CH₂—CH₂— where Y' is CR15 and R15 combines with R11 or R12 to form a phenyl, pyridyl, pyrimidyl, pyrrolyl, pyrazolyl, isoxazolyl, isothiazolyl, imidazolyl, oxazolyl, thiazolyl or triazolyl substituent optionally substituted with 1-3 substituents selected from methoxy, Cl, F, CH₃ and CF₃; preferably R15 combines with R11 or R12 to form a phenyl, pyrrolyl, pyrazolyl or imidazolyl substituent optionally substituted with 1-3 substituents selected from methoxy, Cl, F, CH₃ and CF₃; most preferably R15 combines with R11 or R12 to form a phenyl substituent optionally substituted with 1-3 substituents selected from methoxy, Cl, F, CH₃ and CF₃.

In the present invention it is preferred that Y is selected from —CH₂—Y"—CH₂— where Y" is CR15 and R15 combines with R11 or R12 to form a phenyl, pyridyl, pyrimidyl, pyrrolyl, pyrazolyl, isoxazolyl, isothiazolyl, imidazolyl, oxazolyl, thiazolyl or triazolyl substituent optionally substituted with 1-3 substituents selected from methoxy, Cl, F, CH₃ and CF₃; preferably R15 combines with R11 or R12 to form a phenyl, pyrrolyl, pyrazolyl or imidazolyl substituent optionally substituted with 1-3 substituents selected from methoxy, Cl, F, CH₃ and CF₃; most preferably R15 combines with R11 or R12 to form a phenyl substituent optionally substituted with 1-3 substituents selected from methoxy, Cl, F, CH₃ and CF₃.

In the present invention it is preferred that Y is selected from —CH₂—Y'''—CH₂— where Y''' is NR16 and R16 combines with R11 or R12 to form a pyridyl, pyrimidyl, pyrrolyl, pyrazolyl, isoxazolyl, isothiazolyl, imidazolyl, oxazolyl, thiazolyl or triazolyl substituent optionally substituted with 1-3 substituents selected from methoxy, Cl, F, CH₃ and CF₃; preferably R16 combines with R11 or R12 to form a pyrrolyl, imidazolyl or triazolyl substituent optionally substituted with 1-3 substituents selected from methoxy, Cl, F, CH₃ and CF₃; most preferably R16 combines with R11 or R12 to form a 1,2,3-triazolyl or 1,2,4 triazolyl substituent optionally substituted with 1 substituent selected from methoxy, Cl, F, CH₃ and CF₃.

In the present invention it is preferred that W is CR15 where R15 combines with R11 or R12 to form a phenyl, pyridyl, pyrimidyl, pyrrolyl, pyrazolyl, isoxazolyl, isothiazolyl, imidazolyl, oxazolyl, thiazolyl or triazolyl substituent optionally substituted with 1-3 substituents selected from methoxy, Cl, F, CH₃ and CF₃; preferably R15 combines with R11 or R12 to form a phenyl, pyrrolyl, pyrazolyl or imidazolyl substituent optionally substituted with 1-3 substituents selected from methoxy, Cl, F, CH₃ and CF₃; most preferably R15 combines with R11 or R12 to form a phenyl substituent optionally substituted with 1-3 substituents selected from methoxy, Cl, F, CH₃ and CF₃.

In the present invention it is preferred that W is CR10 where R10 is C(O)NR13R14 and where R13 and R14 are as defined herein.

In the present invention it is preferred that R12 is selected from H, F, Cl, CH₃ and OCH₃, most preferably R12 is H.

In the present invention it is preferred that R13 and R14 are independently selected from H, C₁-C₄ alkyl, aryl, heteroaryl, C₁-C₄ alkylheteroaryl and C₁-C₄ alkylaryl wherein the aryl or heteroaryl substituents are optionally substituted with 1-3 substituents selected from methoxy, Cl, F, CH₃ and CF₃, more preferably R13 and R14 are independently selected from H, methyl, isopropyl, t-butyl, phenyl, benzyl, 1-methyl benzyl and 1,1-dimethyl benzyl wherein phenyl and benzyl substituents are optionally substituted with 1-3 substituents selected from methoxy, Cl, F, CH₃ and CF₃, most preferably R13 is H and R14 is t-butyl.

Where in the present invention R7 and R8 combine to form a substituent it is preferred that R7 and R8 combine to form

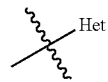

where Het is as defined herein.

In the present invention it is preferred that Het is selected from a pyrrole, pyrazole, imidazole, triazole or tetrazole substituent optionally substituted with 1-3 substituents selected from methoxy, Cl, F, CH₃, CF₃, aryl, heteroaryl, C₁-C₄ alkylaryl and C₁-C₄ alkylheteroaryl; preferably Het is selected from a pyrrolyl, pyrazolyl, imidazolyl or triazolyl substituent optionally substituted with 1-3 substituents selected from methoxy, Cl, F, CH₃, CF₃, aryl, heteroaryl, C₁-C₄ alkylaryl and C₁-C₄ alkylheteroaryl; preferably Het is selected from a pyrazolyl or triazolyl substituent optionally substituted with 1-3 substituent selected from methoxy, Cl, F, CH₃, CF₃, aryl, heteroaryl, C₁-C₄ alkylaryl and C₁-C₄ alkylheteroaryl; more preferrably Het is selected from 1,2,3-triazol-1-yl, 1,2,3-triazol-2-yl and 1,2,4-triazol-1-yl optionally substituted with 1-2 substituents selected from methoxy, Cl, F, CH₃, CF₃, aryl, heteroaryl, C₁-C₄ alkylaryl and C₁-C₄ alkylheteroaryl; most preferably Het is 1,2,4-triazol-1-yl optionally substituted with 1-2 substituents selected from methoxy, Cl, F, CH₃, CF₃, aryl, heteroaryl, C₁-C₄ alkylaryl and C₁-C₄ alkylheteroaryl.

In the present invention it is preferred that Het is selected from a pyrrolyl, pyrazolyl, imidazolyl or triazolyl substituent fused with phenyl, optionally substituted with 1-3 substituents selected from methoxy, Cl, F, $CH_3$ and $CF_3$; preferably Het is selected from a pyrazolyl or triazolyl substituent fused with phenyl, optionally substituted with 1-3 substituent selected from methoxy, Cl, F, $CH_3$ and $CF_3$; more preferably Het is benzotriazol-1-yl, benzotriazol-2-yl, indazol-1-yl, indazol-2-yl or benzimidazol-1-yl optionally substituted with 1-3 substituents selected from methoxy, Cl, F, $CH_3$ and $CF_3$; most preferably Het is benzotriazol-1-yl or benzotriazol-2-yl optionally substituted with 1-3 substituents selected from methoxy, Cl, F, $CH_3$ and $CF_3$.

The compounds of formula I have been found to act as inhibitors of the DPP-IV enzyme in vitro. More particularly the compounds of formula I show selectivity for inhibition of the DPP-IV enzyme over the DPP 8 and/or DPP 9 enzyme.

The present invention provides pharmaceutical compositions comprising a compound of formula I, or a pharmaceutically acceptable salt thereof together with a pharmaceutically acceptable diluent or carrier.

The present invention provides a method for the treatment or prevention of a disorder associated with DPP-IV dysfunction in mammals, which comprises administering a compound of formula I, or a pharmaceutically acceptable salt thereof, to a human being or animal in need thereof.

The present invention also provides a method for the treatment or prevention of a condition selected from type II diabetes, obesity, hyperglycemia and a lipid disorder, which comprises administering a compound of formula I, or a pharmaceutically acceptable salt thereof, to a human being or animal in need thereof.

The present invention further provides a method for the treatment or prevention of a lipid disorder, which comprises administering a compound of formula I, or a pharmaceutically acceptable salt thereof, to a human being or animal in need thereof wherein said lipid disorder is selected from dyslipidemia, hyperlipidemia, hypertriglyceridemia, hypercholesterolemia, low HDL and high LDL.

Further, the present invention provides a compound of formula I, or a pharmaceutically acceptable salt thereof for use as a pharmaceutical; and a compound of formula I, or a pharmaceutically acceptable salt thereof for use in the treatment or prevention of type II diabetes, obesity, hyperglycemia or a lipid disorder.

The present invention also provides a compound of formula I, or a pharmaceutically acceptable salt thereof for use in the treatment or prevention of a lipid disorder, wherein said lipid disorder is selected from dyslipidemia, hyperlipidemia, hypertriglyceridemia, hypercholesterolemia, low HDL and high LDL.

Further, the present invention provides a compound of formula I, or a pharmaceutically acceptable salt thereof for use in the manufacture of a medicament for the treatment or prevention of type II diabetes, obesity, hyperglycemia or a lipid disorder.

The present invention provides a compound of formula I, or a pharmaceutically acceptable salt thereof for use in the manufacture of a medicament for the treatment or prevention of a lipid disorder, wherein said lipid disorder is selected from dyslipidemia, hyperlipidemia, hypertriglyceridemia, hypercholesterolemia, low HDL and high LDL.

As used throughout this specification, it is to be understood that where a group is qualified by "defined herein" or "herein defined" that said group encompasses the first occurring and broadest definition as well as each and all of the particular definitions for that group.

As used herein, the term "halo", unless otherwise stated, designate all four halogens, i.e. F, Cl, Br and I. Preferred halogens are F or Cl, most preferred is F.

As used herein the term "alkyl" includes both straight and branched chain alkyl groups and refers to $C_1$-$C_6$ alkyl chains, preferably $C_1$-$C_4$ alkyl chains.

As used herein, the term "$C_1$-$C_4$ alkyl" includes both straight chain and branched chain alkyl groups, such as methyl, ethyl, propyl, isopropyl, butyl, iso-butyl and t-butyl. Preferred $C_1$-$C_4$ alkyl groups include methyl, ethyl, propyl and isopropyl.

As used herein the term "$C_2$-$C_6$ alkyl" includes both straight chain and branched chain alkyl groups, such as ethyl, propyl, isopropyl, butyl, iso-butyl, t-butyl, pentyl, iso-pentyl, 1,2-dimethylpropyl and hexyl. Preferred $C_2$-$C_6$ alkyl groups include ethyl, propyl, isopropyl, butyl, iso-butyl and t-butyl.

As used herein the term "$C_1$-$C_6$ alkyl" includes both straight chain and branched chain alkyl groups, such as methyl, ethyl, propyl, isopropyl, butyl, iso-butyl, t-butyl, pentyl, iso-pentyl, 1,2-dimethylpropyl and hexyl. Preferred $C_1$-$C_6$ alkyl groups include methyl, ethyl, propyl, isopropyl, butyl, iso-butyl and t-butyl.

As used herein the term "alkoxy" refers to an alkyl group as defined herein linked to an oxygen atom.

As used herein the term "$C_1$-$C_4$ alkoxy" includes methoxy, ethoxy, propoxy, isopropoxy, butoxy, iso-butoxy, t-butoxy. Preferred $C_1$-$C_4$ alkoxy groups include methoxy, ethoxy and isopropoxy.

As used herein the term "$C_1$-$C_6$ alkoxy" includes methoxy, ethoxy, propoxy, isopropoxy, tert-butoxy, pentoxy, iso-pentoxy and 1,2-dimethylpropoxy. Preferred $C_1$-$C_6$ alkoxy groups include methoxy, ethoxy, isopropoxy and tert-butoxy.

As used herein, the term "haloalkyl" refers to an alkyl group as defined herein wherein one or more of the hydrogens is replaced by a halo substituent as defined herein, which replacement can be at any site on the alkyl chain.

As used herein, the term "$C_1$-$C_2$ haloalkyl" includes fluoromethyl, chloromethyl, difluoromethyl, dichloromethyl, trifluoromethyl, fluoroethyl, chloroethyl, 1,2-difluoroethyl, 1,1-difluoroethyl, 1,2-dichloroethyl, 1,1-dichloroethyl, 1,1,1-trifluoromethyl and 1,1,1-trifluoroethyl.

As used herein, the term "$C_1$-$C_4$ haloalkyl" includes fluoromethyl, chloromethyl, difluoromethyl, dichloromethyl, trifluoromethyl, fluoroethyl, chloroethyl, 1,2-difluoroethyl, 1,1-difluoroethyl, 1,2-dichloroethyl, 1,1-dichloroethyl, 1,1,1-trifluoroethyl, 1,1,1-trifluoropropyl and 1,1,1,3,3,3-hexafluoroisopropyl. Preferred $C_1$-$C_4$ haloalkyl groups include fluoromethyl, difluoromethyl, trifluoromethyl, fluoroethyl, 1,2-difluoroethyl, 1,1-difluoroethyl trifluoromethyl 1,2-difluoroethyl, 1,1-difluoroethyl, and 1,1,1-trifluoroethyl, most preferred are fluoromethyl, difluoromethyl and trifluoromethyl.

As used herein, the term "$C_1$-$C_6$ haloalkyl" includes fluoromethyl, chloromethyl, difluoromethyl, dichloromethyl, trifluoromethyl, fluoroethyl, chloroethyl, 1,2-difluoroethyl, 1,1-difluoroethyl, 1,2-dichloroethyl, 1,1-dichloroethyl, 1,1,1-trifluoroethyl, 1,1,1-trifluoropropyl and 1,1,1,3,3,3-hexafluoroisopropyl. Preferred $C_1$-$C_6$ haloalkyl groups include fluoromethyl, difluoromethyl, trifluoromethyl, fluoroethyl, 1,2-difluoroethyl, 1,1-difluoroethyl trifluoromethyl 1,2-difluoroethyl, 1,1-difluoroethyl, and 1,1,1-trifluoroethyl, most preferred are fluoromethyl, difluoromethyl and trifluoromethyl.

As used herein, the term "haloalkoxy" refers to an alkoxy group as defined herein wherein one or more of the hydrogens is replaced by a halo substituent as defined herein, which replacement can be at any site on the alkyl chain.

As used herein, the term "$C_1$ haloalkoxy" includes fluoromethoxy, chloromethoxyl, difluoromethoxy, dichloromethoxy, trifluoromethoxy. Preferred $C_1$ haloalkoxy groups include fluoromethoxy, difluoromethoxy and trifluoromethoxy.

As used herein, the term "$C_1$-$C_4$ haloalkoxy" includes fluoromethoxy, chloromethoxy, difluoromethoxy, dichloromethoxy, trifluoromethoxy, 1,2-difluoroethoxy, 1,1-difluoroethoxy, 1,2-dichloroethoxy, 1,1-dichloroethoxy, 1,1,1-trifluoroethoxy, 1,1,1-trifluoropropoxy and 1,1,1,3,3,3-hexafluoroisopropoxy. Preferred $C_1$-$C_4$ haloalkoxy groups include fluoromethoxy, difluoromethoxy, trifluoromethoxy, 1,2-difluoroethoxy, 1,1-difluoroethoxy and 1,1,1-trifluoroethoxy, most preferred are fluoromethoxy, difluoromethoxy, trifluoromethoxy, 1,2-difluoroethoxy, 1,1-difluoroethoxy and 1,1,1-trifluoroethoxy.

As used herein, the term "$C_1$-$C_6$ haloalkoxy" includes fluoromethoxy, chloromethoxy, difluoromethoxy, dichloromethoxy, trifluoromethoxy, 1,2-difluoroethoxy, 1,1-difluoroethoxy, 1,2-dichloroethoxy, 1,1-dichloroethoxy, 1,1,1-trifluoroethoxy, 1,1,1-trifluoropropoxy and 1,1,1,3,3,3-hexafluoroisopropoxy. Preferred $C_1$-$C_6$ haloalkoxy groups include fluoromethoxy, difluoromethoxy, trifluoromethoxy, 1,2-difluoroethoxy, 1,1-difluoroethoxy and 1,1,1-trifluoroethoxy, most preferred are fluoromethoxy, difluoromethoxy, trifluoromethoxy, 1,2-difluoroethoxy, 1,1-difluoroethoxy and 1,1,1-trifluoroethoxy.

As used herein the term "hydroxy $C_2$-$C_6$ alkyl" refers to a $C_2$-$C_6$ alkyl group as defined herein wherein one of the hydrogens is replaced by an OH substituent, which replacement can be at any site on the alkyl chain, and includes 1-hydroxy ethyl, 2-hydroxy ethyl, 2-hydroxy propyl, 3-hydroxy propyl, 2-hydroxy isopropyl, 3-hydroxy butyl and 4-hydroxy butyl. Preferred hydroxy $C_2$-$C_6$ alkyl groups include ethanol, isopropanol, and n-propanol.

As used herein the term "hydroxy $C_1$-$C_6$ alkyl" refers to a $C_1$-$C_6$ alkyl group as defined herein wherein one of the hydrogens is replaced by an OH substituent, which replacement can be at any site on the alkyl chain, and includes hydroxy methyl, 1-hydroxy ethyl, 2-hydroxy ethyl, 2-hydroxy propyl, 3-hydroxy propyl, 2-hydroxy isopropyl, 3-hydroxy butyl and 4-hydroxy butyl. Preferred hydroxy($C_1$-$C_6$)alkyl groups include methanol, ethanol, isopropanol, and n-propanol.

As used herein the term "$C_1$-$C_4$ alkyl-O—$C_1$-$C_4$ alkyl" refers to a $C_1$-$C_4$ alkyl group as defined herein wherein one of the hydrogens is replaced by an oxygen substituent which replacement can be at any site on the alkyl chain, wherein the oxygen substituent is attached to a further $C_1$-$C_4$ alkyl group as defined herein, and includes methoxymethyl, ethoxymethyl, propoxymethyl, isopropoxymethyl, tert-butoxymethyl, methoxyethyl, ethoxyethyl, propoxyethyl, isopropoxyethyl and tert-butoxyethyl. Preferred $C_1$-$C_4$ alkyl-O—$C_1$-$C_4$ alkyl groups include methoxymethyl, ethoxymethyl, methoxyethyl and ethoxyethyl.

As used herein the term "$C_2$-$C_6$ alkyl-O—$C_1$-$C_6$ alkyl" refers to a $C_2$-$C_6$ alkyl group as defined herein wherein one of the hydrogens is replaced by an oxygen substituent which replacement can be at any site on the alkyl chain, wherein the oxygen substituent is attached to a further $C_2$-$C_6$ alkyl group as defined herein, and includes ethoxymethyl, propoxymethyl, isopropoxymethyl, tert-butoxymethyl, pentoxymethyl, methethoxyethyl, propoxyethyl, isopropoxyethyl, tert-butoxyethyl and pentoxyethyl. Preferred $C_2$-$C_6$ alkyl-O—$C_1$-$C_6$ alkyl groups include ethoxymethyl and ethoxyethyl.

As used herein the term "$C_1$-$C_6$ alkyl-O—$C_1$-$C_6$ alkyl" refers to a $C_1$-$C_6$ alkyl group as defined herein wherein one of the hydrogens is replaced by an oxygen substituent which replacement can be at any site on the alkyl chain, wherein the oxygen substituent is attached to a further $C_1$-$C_6$ alkyl group as defined herein, and includes methoxymethyl, ethoxymethyl, propoxymethyl, isopropoxymethyl, tert-butoxymethyl, pentoxymethyl, methoxyethyl, ethoxyethyl, propoxyethyl, isopropoxyethyl, tert-butoxyethyl and pentoxyethyl. Preferred $C_1$-$C_6$ alkyl-O—$C_1$-$C_6$ alkyl groups include methoxymethyl, ethoxymethyl, methoxyethyl and ethoxyethyl.

As used herein, the term "$C_3$-$C_6$ cycloalkyl" means a monovalent unsubstituted saturated cyclic hydrocarbon radical having from 3 to 6 carbon atoms and includes cyclopropyl, cyclobutyl, cyclohexyl and cyclopentyl. Preferred $C_3$-$C_6$ cycloalkyl are cyclopropyl and cyclohexyl.

As used herein, the term "aryl" refers to a mono- or polycyclic aromatic ring system and includes phenyl, 1-naphthyl and 2-naphthyl. Preferred aryl group is phenyl.

As used herein, the term "$C_1$-$C_4$ alkylaryl" refers to a $C_1$-$C_4$ alkyl group as defined herein wherein one of the hydrogens is replaced by an aryl substituent as defined herein which replacement can be at any site on the alkyl chain, and includes benzyl, phenylethyl, phenylpropyl, 1-methyl benzyl, phenyl butyl, 1,1-dimethyl benzyl, naphthylmethyl, naphthylethyl, naphthylpropyl, naphthylisopropyl, naphthylbutyl, naphthyl-t-butyl. Preferred $C_1$-$C_4$ alkylaryl include benzyl, phenylethyl, 1-methyl benzyl and 1,1-dimethyl benzyl.

As used herein, the term "$C_1$-$C_6$ alkylaryl" refers to a $C_1$-$C_6$ alkyl group as defined herein wherein one of the hydrogens is replaced by an aryl substituent as defined herein which replacement can be at any site on the alkyl chain, and includes benzyl, phenylethyl, phenylpropyl, 1-methyl benzyl, phenyl butyl, 1,1-dimethyl benzyl, naphthylmethyl, naphthylethyl, naphthylpropyl, naphthylisopropyl, naphthylbutyl, naphthyl-t-butyl. Preferred $C_1$-$C_6$ alkylaryl include benzyl, phenylethyl, 1-methyl benzyl and 1,1-dimethyl benzyl.

As used herein the term "heteroaryl" includes both monocyclic and bicyclic aromatic groups and includes 5-6-membered heteroaryl and 8-10-membered bicyclic heteroaryl.

As used herein, the term "5-6-membered heteroaryl" means a monocyclic aromatic group with a total of 5 or 6 atoms in the ring wherein from 1 to 4 of those atoms are each independently selected from N, O and S. Preferred groups have 1, 2 or 3 atoms in the ring which are each independently selected from N, O and S. Examples of 5-membered heteroaryl groups include pyrrolyl (also called azolyl), furanyl, thienyl, pyrazolyl (also called 1H-pyrazolyl and 1,2-diazolyl), imidazolyl, oxazolyl (also called 1,3-oxazolyl), isoxazolyl (also called 1,2-oxazolyl), thiazolyl (also called 1,3-thiazolyl), isothiazolyl (also called 1,2-thiazolyl), triazolyl, oxadiazolyl, thiadiazolyl, tetrazolyl, oxatriazolyl and thiatriazolyl. Examples of 6-membered heteroaryl groups include pyridinyl, pyrimidyl, pyrazinyl, pyridazinyl and triazinyl.

"Pyrrolyl" as used herein includes pyrrol-1-yl, pyrrol-2-yl and pyrrol-3-yl.

"Furanyl" (also called "furyl") as used herein includes furan-2-yl and furan-3-yl (also called 2-furyl and 3-furyl). Furan-2-yl is preferred.

"Thienyl" (also called "thiophenyl") as used herein includes thien-2-yl and thien-3-yl (also called 2-thiophenyl and 3-thiophenyl).

"Pyrazolyl" as used herein includes pyrazol-1-yl, pyrazol-3-yl, pyrazol-4-yl and pyrazol-5-yl (also called 1-pyrazole, 3-pyrazole, 4-pyrazole and 5-pyrazole). Pyrazol-1-yl is preferred.

"Imidazolyl" as used herein includes imidazol-1-yl, imidazol-2-yl, imidazol-4-yl and imidazol-5-yl. Imidazol-1-yl and imidazol-2-yl are preferred.

"Oxazolyl" as used herein includes oxazol-2-yl, oxazol-4-yl and oxazol-5-yl.

"Isoxazolyl" as used herein includes isoxazol-3-yl, isoxazol-4-yl, and isoxazol-5-yl.

"Thiazolyl" as used herein includes thiazol-2-yl, thiazol-4-yl and thiazol-5-yl (also called 2-thiazolyl, 4-thiazolyl and 5-thiazolyl).

"Isothiazolyl" as used herein includes isothiazol-3-yl, isothiazol-4-yl, and isothiazol-5-yl.

"Triazolyl" as used herein includes 1,2,3-triazol-1-yl, 1,2,3-triazol-2-yl, 1,2,3-triazol-4-yl, 1,2,3-triazol-5-yl, 1,2,4-triazol-1-yl, 1,2,4-triazol-3-yl and 1,2,4-triazol-5-yl. 1,2,3-triazol-1-yl, 1,2,3-triazol-2-yl and 1,2,4-triazol-1-yl are preferred.

"Oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl.

"Thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl.

"Tetrazolyl" as used herein includes tetrazol-1-yl and tetrazol-5-yl.

"Oxatriazolyl" as used herein includes 1,2,3,4-oxatriazol-5-yl and 1,2,3,5-oxatriazol-4-yl.

"Thiatriazolyl" as used herein includes 1,2,3,4-thiatriazol-5-yl and 1,2,3,5-thiatriazol-4-yl.

"Pyridinyl" (also called "pyridyl") as used herein includes pyridin-2-yl, pyridin-3-yl and pyridin-4-yl (also called 2-pyridyl, 3-pyridyl and 4-pyridyl).

"Pyrimidyl" as used herein includes pyrimid-2-yl, pyrimid-4-yl, pyrimid-5-yl and pyrimid-6-yl.

"Pyridazinyl" as used herein includes pyridazin-3-yl and pyridazin-4-yl.

"Pyrazinyl" as used herein includes pyrazin-2-yl and pyrazin-3-yl.

"Triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl.

As used herein, the term "8-10-membered bicyclic heteroaryl" means a fused bicyclic aromatic group with a total of 8, 9 or 10 atoms in the ring system wherein from 1 to 4 of those atoms are each independently selected from N, O and S. Preferred groups have from 1 to 3 atoms in the ring system which are each independently selected from N, O and S. Suitable 8-membered bicyclic heteroaryl groups include imidazo[2,1-b][1,3]thiazolyl, thieno[3,2-b]thienyl, thieno[2,3-d][1,3]thiazolyl and thieno[2,3-d]imidazolyl. Suitable 9-membered bicyclic heteroaryl groups include indolyl, isoindolyl, benzofuranyl (also called benzo[b]furanyl), isobenzofuranyl (also called benzo[c]furanyl), benzothienyl (also called benzo[b]thienyl), isobenzothienyl (also called benzo[c]thienyl), indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl and imidazo[1,2-a]pyridine. Suitable 10-membered bicyclic heteroaryl groups include quinolinyl, isoquinolinyl, cinnolinyl, quinazolinyl, quinoxalinyl, 1,5-naphthyridyl, 1,6-naphthyridyl, 1,7-naphthyridyl and 1,8-naphthyridyl.

"Imidazo[2,1-b][1,3]thiazolyl" as used herein includes imidazo[2,1-b][1,3]thiazol-2-yl, imidazo[2,1-b][1,3]thiazol-3-yl, imidazo[2,1-b][1,3]thiazol-5-yl and imidazo[2,1-b][1,3]thiazol-6-yl.

"Thieno[3,2-b]thienyl" as used herein includes thieno[3,2-b]thien-2-yl, thieno[3,2-b]thien-3-yl, thieno[3,2-b]thien-5-yl and thieno[3,2-b]thien-6-yl.

"Thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl.

"Thieno[2,3-d]imidazolyl" as used herein includes thieno[2,3-d]imidazol-2-yl, thieno[2,3-d]imidazol-4-yl and thieno[2,3-d]imidazol-5-yl.

"Indolyl" as used herein includes indol-1-yl, indol-2-yl, indol-3-yl, indol-4-yl, indol-5-yl, indol-6-yl and indol-7-yl.

"Isoindolyl" as used herein includes isoindol-1-yl, isoindol-2-yl, isoindol-3-yl, isoindol-4-yl, isoindol-5-yl, isoindol-6-yl and isoindol-7-yl.

"Benzofuranyl" as used herein includes benzofuran-2-yl, benzofuran-3-yl, benzofuran-4-yl, benzofuran-5-yl, benzofuran-6-yl and benzofuran-7-yl.

"Isobenzofuranyl" as used herein includes isobenzofuran-1-yl, isobenzofuran-3-yl, isobenzofuran-4-yl, isobenzofuran-5-yl, isobenzofuran-6-yl and isobenzofuran-7-yl.

"Benzothienyl" (also called "benzothiophenyl") as used herein includes benzothien-2-yl, benzothien-3-yl, benzothien-4-yl, benzothien-5-yl, benzothien-6-yl and benzothien-7-yl (also called 2-benzo[b]thiophenyl, 3-benzo[b]thiophenyl, 4-benzo[b]thiophenyl, 5-benzo[b]thiophenyl, 6-benzo[b]thiophenyl and 7-benzo[b]thiophenyl).

"Isobenzothienyl" as used herein includes isobenzothien-1-yl, isobenzothien-3-yl, isobenzothien-4-yl, isobenzothien-5-yl, isobenzothien-6-yl and isobenzothien-7-yl.

"Indazolyl" as used herein includes indazol-1-yl, indazol-3-yl, indazol-4-yl, indazol-5-yl, indazol-6-yl and indazol-7-yl. Indazol-1-yl is preferred.

"Benzimidazolyl" as used herein includes benzimidazol-1-yl, benzimidazol-2-yl, benzimidazol-4-yl, benzimidazol-5-yl, benzimidazol-6-yl and benzimidazol-7-yl. Benzimidazol-1-yl is preferred "1,3-Benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl.

"1,2-Benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl.

"2,1-Benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl.

"1,3-Benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl.

"1,2-Benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl.

"2,1-Benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl.

"Benzotriazolyl" as used herein includes benzotriazol-1-yl, benzotriazol-4-yl, benzotriazol-5-yl, benzotriazol-6-yl and benzotriazol-7-yl. Benzotriazol-1-yl is preferred.

"1,2,3-Benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl.

"2,1,3-Benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl.

"1,2,3-Benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl.

"2,1,3-Benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl.

"Thienopyridinyl" as used herein includes thieno[2,3-b]pyridinyl, thieno[2,3-c]pyridinyl, thieno[3,2-c]pyridinyl and thieno[3,2-b]pyridinyl.

"Purinyl" as used herein includes purin-2-yl, purin-6-yl, purin-7-yl and purin-8-yl.

"Imidazo[1,2-a]pyridinyl" as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl.

"Quinolinyl" as used herein includes quinolin-2-yl, quinolin-3-yl, quinolin-4-yl, quinolin-5-yl, quinolin-6-yl, quinolin-7-yl and quinolin-8-yl.

"Isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl.

"Cinnolinyl" as used herein includes cinnolin-3-yl, cinnolin-4-yl, cinnolin-5-yl, cinnolin-6-yl, cinnolin-7-yl and cinnolin-8-yl.

"Quinazolinyl" as used herein includes quinazolin-2-yl, quinazolin-4-yl, quinazolin-5-yl, quinazolin-6-yl, quinazolin-7-yl and quinazolin-8-yl.

"1,4-Naphthyridyl" as used herein includes 1,4-naphthyrid-2-yl, 1,4-naphthyrid-3-yl, 1,4-naphthyrid-5-yl, 1,4-naphthyrid-6-yl, 1,4-naphthyrid-7-yl and 1,4-naphthyrid-8-yl.

"1,5-Naphthyridyl" as used herein includes 1,5-naphthyrid-2-yl, 1,5-naphthyrid-3-yl, 1,5-naphthyrid-4-yl, 1,5-naphthyrid-6-yl, 1,5-naphthyrid-7-yl and 1,5-naphthyrid-8-yl.

"1,6-Naphthyridyl" as used herein includes 1,6-naphthyrid-2-yl, 1,6-naphthyrid-3-yl, 1,6-naphthyrid-4-yl, 1,6-naphthyrid-5-yl, 1,6-naphthyrid-7-yl and 1,6-naphthyrid-8-yl.

"1,7-Naphthyridyl" as used herein includes 1,7-naphthyrid-2-yl, 1,7-naphthyrid-3-yl, 1,7-naphthyrid-4-yl, 1,7-naphthyrid-5-yl, 1,7-naphthyrid-6-yl and 1,7-naphthyrid-8-yl.

"1,8-Naphthyridyl" as used herein includes 1,8-naphthyrid-2-yl, 1,8-naphthyrid-3-yl, 1,8-naphthyrid-4-yl, 1,8-naphthyrid-5-yl, 1,8-naphthyrid-6-yl and 1,8-naphthyrid-7-yl.

As used herein, the term "$C_1$-$C_4$ alkylheteroaryl" refers to a $C_1$-$C_4$ alkyl group as defined herein wherein one of the hydrogens is replaced by a heteroaryl substituent as defined herein which replacement can be at any site on the alkyl chain, and includes thiophenylmethyl, thiophenylethyl, thiophenylpropyl, thiophenylbutyl furanylmethyl, furanylethyl, furanylpropyl, furanylbutyl, pyrrolylmethyl, pyrrolylethyl, pyrrolylpropyl, pyrrolylbutyl, imidazolylmethyl, imidazolylethyl, imidazolylpropyl, imidazolylbutyl, triazolylmethyl, triazolylethyl, triazolylpropyl, triazolylbutyl, pyridinylmethyl, pyridinylethyl, pyridinylpropyl, pyridinylbutyl, quinolinylmethyl, quinolinylethyl, quinolinylpropyl and quinolinylbutyl. Preferred $C_1$-$C_4$ alkylheteroaryl include thiophenylmethyl, thiophenylethyl, furanylmethyl, furanylethyl, imidazolylmethyl, imidazolylethyl, triazolylmethyl and triazolylethyl.

As used herein, the term "$C_1$-$C_6$ alkylheteroaryl" refers to a $C_1$-$C_6$ alkyl group as defined herein wherein one of the hydrogens is replaced by a heteroaryl substituent as defined herein which replacement can be at any site on the alkyl chain, and includes thiophenylmethyl, thiophenylethyl, thiophenylpropyl, thiophenylbutyl furanylmethyl, furanylethyl, furanylpropyl, furanylbutyl, pyrrolylmethyl, pyrrolylethyl, pyrrolylpropyl, pyrrolylbutyl, imidazolylmethyl, imidazolylethyl, imidazolylpropyl, imidazolylbutyl, triazolylmethyl, triazolylethyl, triazolylpropyl, triazolylbutyl, pyridinylmethyl, pyridinylethyl, pyridinylpropyl, pyridinylbutyl, quinolinylmethyl, quinolinylethyl, quinolinylpropyl and quinolinylbutyl. Preferred $C_1$-$C_6$ alkylheteroaryl include thiophenylmethyl, thiophenylethyl, furanylmethyl, furanylethyl, imidazolylmethyl, imidazolylethyl, triazolylmethyl and triazolylethyl.

As used herein, the term "N-linked 5-membered heteroaryl" refers to a monocyclic aromatic group with a total of 5 atoms in the ring wherein from 1 to 4 of those atoms are N. Preferred groups have 1, 2 or 3 atoms in the ring which are each N. Examples of N-linked 5-membered heteroaryl rings include pyrrolyl (also called azolyl), pyrazolyl (also called 1H-pyrazolyl and 1,2-diazolyl), imidazolyl, triazolyl and tetrazolyl. Preferred N-linked 5-membered heteroaryl rings include pyrazol-1-yl, imidazol-1-yl, 1,2,3-triazol-1-yl, 1,2,3-triazol-2-yl and 1,2,4-triazol-1-yl, more preferred are 1,2,3-triazol-1-yl, 1,2,3-triazol-2-yl and 1,2,4-triazol-1-yl, most preferred is 1,2,4-triazol-1-yl.

As used herein the term "heterocycle" refers to a saturated ring having from 4 to 8 atoms and preferably 5 or 6 atoms which incorporate the N atom of R9, optionally having one or two additional heteroatoms selected from oxygen, sulfur and nitrogen, the remaining atoms being carbon.

As used herein the term "4-8 membered heterocycle" include azetidine, pyrrolidine, piperidine, piperizine, morpholine and thiomorpholine.

The compounds of the present invention may be chiral, and it is intended that any enantiomers, as separated, pure or partially purified enantiomers or racemic mixtures thereof are included within the scope of the invention. Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms, which the compounds are able to form, are included within the scope of the present invention. Thus, as one skilled in the art knows, certain aryls may exist in tautomeric forms. The invention also includes tautomers, enantiomers and other stereoisomers of the compounds of formula I. Such variations are contemplated to be within the scope of the invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The designation ⎯ refers to a bond that protrudes forward out of the plane of the page. The designation ⋯⋯ refers to a bond that protrudes backward out of the plane of the page.

The compounds of formula I, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of formula I may be obtained by stereospecific synthesis using optically pure starting materials or reagents of known configuration or through enantioselective synthesis.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 - E^2} \times 100$$

wherein E1 is the amount of the first enantiomer and E2 is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "Enantiomers. Racemates, and Resolutions," John Wiley and Sons, Inc., 1981, and E. L. Eliel and S. H. Wilen, "Stereochemistry of Organic Compounds," (Wiley-Interscience 1994). Examples of resolutions include recrystallization techniques or chiral chromatography.

Formula I, Ia and Ib show the structure of the compounds of the present invention without preferred stereochemistry. Preferred stereochemistry of the compounds of the present invention are indicated by the compounds of formula II, IIa and IIb. Most preferred stereochemistry of the compounds of the present invention are indicated by the compounds of formula III, IIIa and IIIb.

Preferred compounds of the present invention include (2S,3R)-3-Amino-4-phenyl-1-[1,2,3]triazol-1-yl-butan-2-ol, (2S,3R)-3-Amino-4-phenyl-1-[1,2,3]triazol-2-yl-butan-2-ol, (2S,3R)-3-Amino-4-phenyl-1-[1,2,4]triazol-1-yl-butan-2-ol, (2S,3R)-3-Amino-4-phenyl-1-([3R,S]-3-phenyl-pyrrolidin-1-yl)-butan-2-ol, (2S,3R)-3-Amino-4-phenyl-1-(4-phenyl-piperidin-1-yl)-butan-2-ol, (2S,3R)-3-Amino-4-phenyl-1-([3R,S]-3-phenyl-piperidin-1-yl)-butan-2-ol, (2S)-1-[(2S,3R)-3-Amino-2-hydroxy-4-phenyl-butyl]-pyrrolidine-2-carboxylic acid amide, 2S,3R)-3-Amino-1-benzotriazol-1-yl-4-phenyl-butan-2-ol, (2S,3R)-3-Amino-1-benzotriazol-2-yl-4-phenyl-butan-2-ol, (2S)-1-[(2S,3R)-3-Amino-2-hydroxy-4-phenyl-butyl]-pyrrolidine-2-carboxylic acid ethylamide, (2S,3R)-3-Amino-1-indazol-1-yl-4-phenyl-butan-2-ol, (2S,3R)-3-Amino-1-indazol-2-yl-4-phenyl-butan-2-ol, (2S,3R)-3-Amino-4-phenyl-1-pyrazol-1-yl-butan-2-ol, (2S,3R)-3-Amino-1-imidazol-1-yl-4-phenyl-butan-2-ol, (2S,3R)-3-Amino-1-benzimidazol-1-yl-4-phenyl-butan-2-ol, 2S,3R)-3-Amino-1-[(2S)-2-(4-fluorophenyl)-pyrrolidin-1-yl]-4-phenyl-butan-2-ol, (2S,3R)-3-Amino-4-phenyl-1-([2S]-2-phenyl-pyrrolidin-1-yl)-butan-2-ol, (2S,3R)-3-Amino-4-phenyl-1-([2R]-2-phenyl-pyrrolidin-1-yl)-butan-2-ol, (2S,3R)-3-Amino-1-([2S]-2-methyoxymethyl-pyrrolidin-1-yl)-4-phenyl-butan-2-ol, (2S,3R)-3-Amino-1-([2S]-2-hydroxymethyl-pyrrolidin-1-yl)-4-phenyl-butan-2-ol, (2S,3R)-3-Amino-1-methylamino-4-phenyl-butan-2-ol, N-[(2S,3R)-3-Amino-2-hydroxy-4-phenyl-butyl]-N-methyl-methanesulfonamide, N-[(2S,3R)-3-Amino-2-hydroxy-4-phenyl-butyl]-N-methyl-benzamide, N-[(2S,3R)-3-Amino-2-hydroxy-4-phenyl-butyl]-N-methyl-acetamide,S)-1-([2S,3R]-3-Amino-2-hydroxy-4-phenyl-butyl)-pyrrolidine-2-carboxylic acid tert-butylamide, (2S,3R)-3-Amino-1-(methyl-phenethylamino)-4-phenyl-butan-2-ol, (2S,3R)-3-Amino-1-phenethylamino-4-phenyl-butan-2-ol, (2S,3R)-3-Amino-1-benzylamino-4-phenyl-butan-2-ol, (2S,3R)-3-Amino-1-dimethylamino-4-phenyl-butan-2-ol, (2S,3R)-3-Amino-1-(benzyl-methylamino)-4-phenyl-butan-2-ol, (2S,3R)-3-Amino-1-(1,3-dihydro-isoindol-2-yl)-4-phenyl-butan-2-ol, (2S,3R)-3-Amino-4-phenyl-1-(3-trifluoromethyl-5,6-dihydro-8H-[1,2,4]triazolo[4,3-a]pyrazin-7-yl)-butan-2-ol, (2S,3R)-3-Amino-1-(3,4-dihydro-1H-isoquinolin-2-yl)-4-phenyl-butan-2-ol, (2S,3R)-3-Amino-4-phenyl-1-piperidin-1-yl-butan-2-ol, (2S,3R)-3-Amino-4-phenyl-1-pyrrolidin-1-yl-butan-2-ol, (2S,3R)-3-Amino-1-morpholin-4-yl-4-phenyl-butan-2-ol, (S)-1-([2S,3R]-3-Amino-2-hydroxy-4-[2,5-difluoro-phenyl]-butyl)-pyrrolidine-2-carboxylic acid tert-butylamide, (2S,3R)-3-Amino-4-(2,5-difluoro-phenyl)-1-pyrrolidin-1-yl-butan-2-ol, (2S,3R)-3-Amino-1-(3,4-dihydro-1H-isoquinolin-2-yl)-4-(2,5-difluoro-phenyl)-butan-2-ol and N-[(2S,3R)-3-Amino-2-hydroxy-4-(2,5-difluoro-phenyl)-butyl]-N-methyl-acetamide or a pharmaceutically acceptable salt thereof.

In general, the term "pharmaceutical" when used as an adjective means substantially non-toxic to living organisms. For example, the term "pharmaceutical salt" as used herein, refers to salts of the compounds of formula I which are substantially non-toxic to living organisms. See, e.g., Berge, S. M, Bighley, L. D., and Monkhouse, D. C., "Pharmaceutical Salts," J. Pharm. Sci., 66:1, 1977. The present invention also encompasses pharmaceutically acceptable salts of the present compounds. Such salts include pharmaceutically acceptable acid addition salts, pharmaceutically acceptable metal salts, ammonium and alkylated ammonium salts. Also intended as pharmaceutically acceptable acid addition salts are any hydrates that the present compounds are able to form. Furthermore, the pharmaceutically acceptable salts comprise basic amino acid salts. Typical pharmaceutical salts include those salts prepared by reaction of the compounds of formula I with an inorganic or organic acid. Such salts are known as acid addition salts. These pharmaceutical salts frequently have enhanced solubility characteristics compared to the compound from which they are derived, and thus are often more amenable to formulation as liquids or emulsions.

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., J. Pharm. Sci., 66:1, 1977. Since compounds of this invention can be basic in nature, they accordingly react with any of a number of inorganic and organic acids to form pharmaceutical acid addition salts. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The pharmaceutical salts of the invention are typically formed by reacting a compound of formula I with an equimolar or excess amount of acid or base. The reactants are generally combined in a mutual solvent such as diethylether, tetrahydrofuran, methanol, ethanol, isopropanol, benzene, and the like for acid addition salts.

Preferred pharmaceutical acid addition salts are hydrochloric acid and the like.

The compounds of the present invention may form solvates with standard low molecular weight solvents using methods well known to the person skilled in the art. Such solvates are also contemplated as being within the scope of the present invention.

The compounds of the present invention are useful in the treatment or prevention of the following conditions or diseases: hyperglycaemia, low glucose tolerance, insulin resistance, obesity, lipid disorders, dyslipidemia, hyperlipidemia, hypertriglyceridema, hypercholesterolemia, low HDL levels, high LDL levels, atherosclerosis and its sequelae, vascular restenosis, irritable bowel syndrome, inflammatory bowel disease, Crohn's disease, ulcerative colitis, other inflammatory conditions, pancreatitis, abdominal obesity, neurodegenerative disease, retinopathy, nephropathy, neuropathy, Syndrome X, polycystic ovarian syndrome, Type II diabetes, growth hormone deficiency, neutropenia, neuronal disorders, tumor metastasis, benign prostatic hypertrophy, hypertension, osteoporosis and other conditions that may be treated or prevented by inhibition of DPP-IV.

In a further aspect of the invention the present compounds are administered in combination with one or more further active substances. Such further active substances may for example be selected from antidiabetics, antiobesity agents, antihypertensive agents, agents for the treatment of complications resulting from or associated with diabetes and agents for the treatment of complications and disorders resulting from or associated with obesity. The following listing sets out several groups of combinations.

Thus, in a further aspect of the invention the present compounds may be administered in combination with one or more antidiabetics. Suitable antidiabetic agents include insulin, insulin analogues and derivatives such as those disclosed in EP 792 290 (Novo Nordisk A/S), for example $N^{\epsilon B29}$-tetradecanoyl des (B30) human insulin, EP 214 826 and EP 705 275 (Novo Nordisk A/S), for example $Asp^{B28}$ human insulin, U.S. Pat. No. 5,504,188 (Eli Lilly), for example $Lys^{B28}$ $Pro^{B29}$ human insulin, EP 368 187 (Aventis), for example Lantus®, which are all incorporated herein by reference, GLP-1 and GLP-1 derivatives such as those disclosed in WO 98/08871 (Novo Nordisk A/S), which is incorporated herein by reference, as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues, such as glimepiride, α-glucosidase inhibitors, agents acting on the ATP-dependent potassium channel of the β-cells for example potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1, GLP-1 mimetics and GLP-1 receptor agonists such as those disclosed in WO00/42026 and WO0059887, other DPP-IV inhibitors such as isoleucine thiazolidide (P32/98), NVP-DPP-728, LAF 237, P93/01, MK-0431 (Sitagliptin), and BMS 477118, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman La Roche) or those disclosed in WO 03/00262, WO 03/00267 and WO 03/15774 (AstraZeneca), which are incorporated herein by reference, GSK-3 (glycogen synthase kinase-3) inhibitors, compounds modifying the lipid metabolism such as antilipidemic agents such as HMG CoA inhibitors (statins), compounds lowering food intake, PPAR (Peroxisome proliferator-activated receptor) ligands including the PPAR-alpha, PPAR-gamma and PPAR-delta subtypes, and RXR (retinoid X receptor) agonists, such as ALRT-268, LG-1268 or LG-1069

In another aspect of the invention, the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix preparation comprising one or more of these.

In a further aspect of the invention the present compounds are administered in combination with a sulphonylurea such as glibenclamide, glipizide, tolbautamide, chloropamidem, tolazamide, glimepride, glicazide and glyburide.

In another aspect of the invention the present compounds are administered in combination with a biguanidine for example metformin.

In yet another aspect of the invention the present compounds are administered in combination with a meglitinide for example repaglinide or nateglinide.

In still another aspect of the invention the present compounds are administered in combination with a thiazolidinedione insulin sensitizer for example troglitazone, ciglitazone, piolitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another aspect of the invention the present compounds may be YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/63153, WO 63196, WO 00/63209, WO 00/63190 and WO 00/63189 (Novo Nordisk A/S), which are incorporated herein by reference.

In a further aspect of the invention the present compounds are administered in combination with an α-glucosidase inhibitor for example voglibose, emiglitate, miglitol or acarbose.

In another aspect of the invention the present compounds are administered in combination with an agent acting on the ATP-dependent potassium channel of the β-cells for example tolbutamide, glibenclamide, glipizide, glicazide, BTS-67582 or repaglinide.

In yet another aspect of the invention the present compounds may be administered in combination with nateglinide.

In still another aspect of the invention the present compounds are administered in combination with an antilipidemic agent or antihyperlipidemic agent for example cholestyramine, colestipol, clofibrate, gemfibrozil, lovastatin, pravastatin, simvastatin, pitavastatin, rosuvastatin, probucol, dextrothyroxine, fenofibrate oratorvastin.

In still another aspect of the invention the present compounds are administered in combination with compounds lowering food intake.

In another aspect of the invention, the present compounds are administered in combination with more than one of the above-mentioned compounds for example in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

In a further aspect of the invention the present compounds may be administered in combination with one or more anti-obesity agents or appetite regulating agents. Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140 MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor (such as axokine), cannaboid receptor antagonist for example CB-1 (such as rimonabant).

In another aspect of the invention the antiobesity agent is dexamphetamine or amphetamine.

In another aspect of the invention the antiobesity agent is leptin.

In another aspect of the invention the antiobesity agent is fenfluramine or exfenfluramine.

In still another aspect of the invention the antiobesity agent is sibutramine.

In a further aspect of the invention the antiobesity agent is orlistat.

In another aspect of the invention the antiobesity agent is mazindol or phentermine.

In still another aspect of the invention the antiobesity agent is phendimetrazine, diethylpropion, fluoxetine, bupropion, topiramate or ecopipam.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

The compounds of the present invention may be administered in combination with FAS inhibitors.

The compounds of the present invention may also be administered in combination with chemical uncouplers, hormone sensitive lipase inhibitor, imidazolines, 11-β-hydroxysteroid dehydrogenase inhibitors, lipoprotein lipase activator, AMPK activators, immunosuppresive drugs, nicotinamide, ASIS, anti-androgens or carboxypeptidase inhibitors.

It should be understood that any suitable combination of the compounds according to the invention with diet and/or exercise, one or more of the above-mentioned compounds and optionally one or more other active substances are considered to be within the scope of the present invention.

The compounds of formula I can be prepared by one of ordinary skill in the art following a variety of procedures, some of which are illustrated in the procedures and schemes set forth below. The particular order of steps required to produce the compounds of formula I is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of formula I may be further purified, if desired by common techniques such as recrystallization or chromatography over solid supports such as silica gel or alumina.

Suitable protecting groups include those described in T. W. Greene, "Protective Groups in Organic Synthesis", John Wiley and Sons, New York, N.Y., 1991, hereafter referred to as "Greene". Greene indicates appropriate conditions for "protection" and "deprotection" of suitable protecting groups to be used by the skilled artisan.

The skilled artisan will appreciate that not all substituents are compatible with all reaction conditions. These compounds may be protected or modified at a convenient point in the synthesis by methods well known in the art.

The compounds of the present invention may be prepared as is shown in the following reaction schemes.

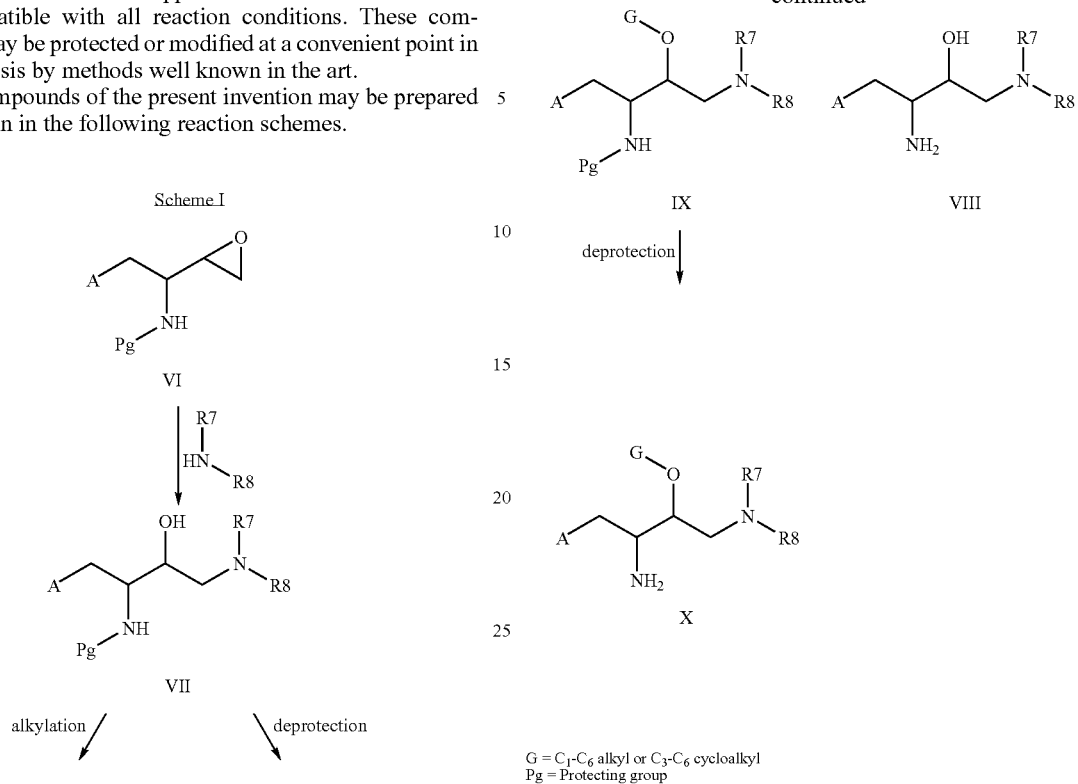

G = C$_1$-C$_6$ alkyl or C$_3$-C$_6$ cycloalkyl
Pg = Protecting group

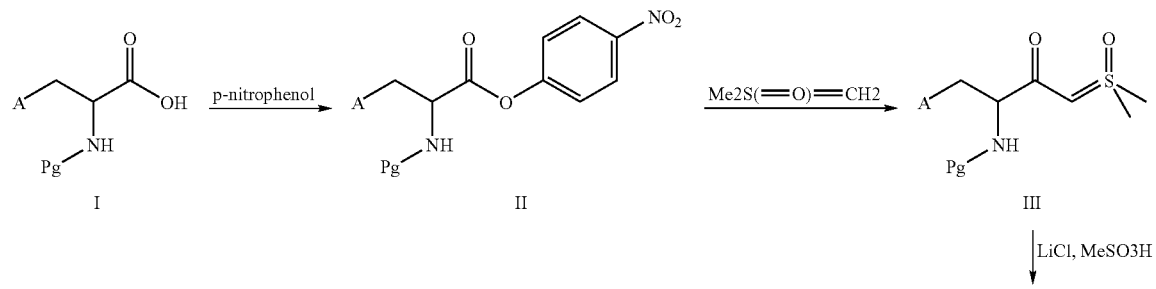

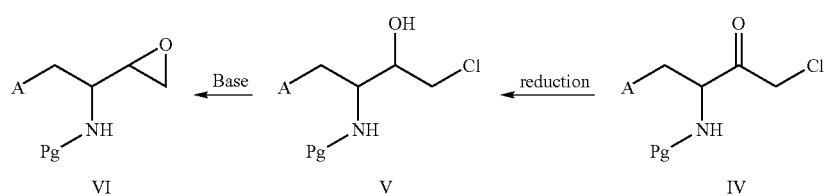

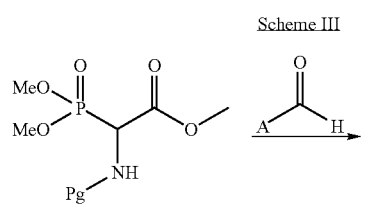

Scheme V

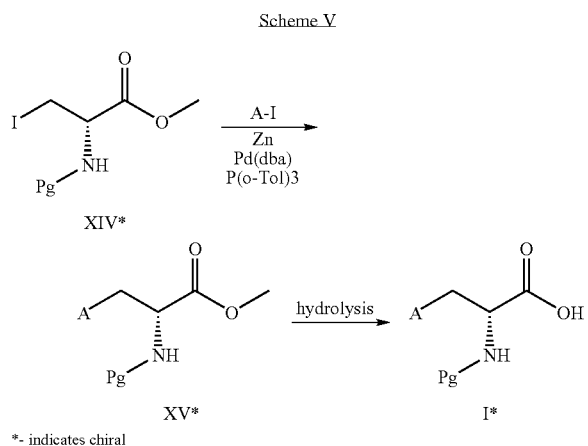

*- indicates chiral

The intermediate XV* of Scheme V is prepared according to the method described in Organic Syntheses, 2004, vol 81, 77.

EXPERIMENTAL SECTION

Abbreviations used follow IUPAC-IUB nomenclature. Additional abbreviations are aq., aqueous; equiv, (molar) equivalent; HPLC, high-performance liquid chromatography; THF, tetrahydrofuran; HOAc, acetic acid; DMSO, dimethyl sulfoxide (perdeuterated if for NMR); EtOAc, ethyl acetate; EtOH, ethanol; MeOH, methanol; DMF, dimethylformamide; DBU, 1,8-diazabicyclo[5.4.0]undec-7-ene; HOBT, 1-hydroxy benzotriazole; EDCI, 1-(3-dimethylaminopropyl)-3-ethylcarbodiimide hydrochloride; LDA, lithium diisopropylamide; TMEDA, N,N,N',N'-tetramethylethylenediamine; AIBN, 2,2'-azobisisobutyronitrile; Boc, tertiary-butyloxy-carbonyl; Cbz, benzyloxy-carbonyl; MS, electrospray mass spectrum; TFA, trifluoroacetic acid; (R,R)-Et-DU-PHOS-Rh, bis-((2R,5R)-2,5-diethylphospholano)-benzene-(cyclooctadiene)-rhodium(I) tetrafluoroborate or trifluoromethanesulfonate salt. All solution concentrations are expressed as % volume/% volume unless otherwise stated. Reagents were obtained from a variety of commercial sources. $^1$HNMR means a proton magnetic resonance spectrum was obtained.

General Reaction Procedures
General Epoxide Opening Procedures
General Procedure 1

To a solution of epoxide (1 equiv) in MeOH (0.2-0.5 M) is added the amine nucleophile (1-5 equiv). After stirring 1-24 h at 50° C., the solvent is removed under reduced pressure. The residue is then partitioned between water and a suitable organic solvent, dried over sodium sulfate and concentrated under reduced pressure to give the product, which can be purified if necessary by silica gel chromatography.

General Procedure 2

To a solution of epoxide (1 equiv) in EtOH (0.2-0.5 M) is added the amine nucleophile (1-5 equiv). After stirring 4-24 h at 75° C., the solvent is removed under reduced pressure. The residue is then partitioned between water and a suitable organic solvent, dried over sodium sulfate and concentrated under reduced pressure to give the product, which can be purified if necessary by silica gel chromatography.

General Procedure 3

To a solution of epoxide (1 equiv) in EtOH (0.2-0.5 M) is added the amine nucleophile (1-2 equiv) and Cs$_2$CO$_3$ (0.2 equiv). After stirring 16-24 h at 40° C., the solvent is removed under reduced pressure. The residue is then partitioned between water and a suitable organic solvent, dried over sodium sulfate and concentrated under reduced pressure to give the product, which can be purified if necessary by silica gel chromatography.

General Procedure 4

To a solution of epoxide (1 equiv) in EtOH (0.2-0.5 M) is added the amine nucleophile (1.1 equiv) and Cs$_2$CO$_3$ (0.2 equiv). The solution is stirred for 28 min at 90° C. in a microwave reactor, and then the solvent is removed under reduced pressure. The residue is then partitioned between water and a suitable organic solvent, dried over sodium sulfate and concentrated under reduced pressure to give the product, which can be purified if necessary by silica gel chromatography.

General Procedure for the Acylation/Sulfonylation
General Procedure 5

To a solution of amine (1 equiv) and diisopropylethylamine (4 equiv) in dichloromethane (0.025-0.1 M) is added an acyl halide or sulfonyl halide (1 equiv), and is stirred or shaken 0.5-1 h at 20° C. The reaction mixture is washed sequentially with water, saturated NaHCO$_3$ (aq), water, 1.0M citric acid (aq) and brine. The organic phase is then dried over sodium sulfate and concentrated under reduced pressure to give the product, which can be purified if necessary by silica gel chromatography.

General Procedure for the Hydrolysis of Carbamate-Protected Amino Esters
General Procedure 6

To a solution of ester (1 equiv) in a solution of 3:1 THF: methanol (0.1 M) or 3:1 THF:water (0.1 M) is added lithium hydroxide (3 equiv) as either a solid or as a 1.0 N aqueous solution. After stirring for 0.1 to 6 h, the reaction mixture is partially concentrated under reduced pressure to remove organic solvents. The resulting aqueous solution is washed with a suitable organic solvent such as ethyl acetate, cooled to 0° C., and then acidified to pH~4 with 1.0 N HCl (aq). The product is then extracted into a suitable organic solvent, which is then dried over sodium or magnesium sulfate, filtered, and concentrated under reduced pressure to give the product, which can be purified if necessary by silica gel chromatography.

General Deprotection Procedures
General Procedure 7:

Into a solution of Boc-protected amine in a suitable non-protic organic solvent (0.01-0.5M) at 0° C.-room temperature is added a solution of HCl (1.0 M in diethyl ether or p-dioxane) and stirred for 20-45 min. Removal of the solvent under reduced pressure provides the product, which can be purified if necessary by either normal or reverse-phase chromatography.

General Procedure 8:

Through a solution of Boc-protected amine in a suitable non-protic organic solvent (0.01-0.5M) at 0° C.-room temperature is bubbled HCl gas for 5-15 min. Removal of the solvent under reduced pressure provides the product, which can be purified if necessary by either normal or reverse-phase chromatography.

General Procedure 9:

To a solution of Boc-protected amine in dichloromethane (0.1-1 M) is added trifluoroacetic acid (1:3 v/v with dichloromethane solvent). After stirring for 1-20 h the solvent is concentrated under reduced pressure and the residue is dissolved in methanol. The resulting solution is applied to an SCX cartridge and then the cartridge is washed with MeOH. The neutral amine is then eluted from the column with 2M NH$_3$ in MeOH and then concentrated under reduced pressure.

The resultant material is dissolved in methanol or ether, HCl (slight excess of a 1N solution in ether or dioxane) is added, and the mixture is concentrated under reduced pressure or filtered to provide the product. If necessary, the product can be purified, either before or after HCl salt formation, by either normal or reverse phase chromatography.

General Procedure 10:

To a solution of Boc-protected amine in dichloromethane (0.1-1 M) is added anisole (2 equiv), followed by trifluoroacetic acid (1:3 v/v with dichloromethane solvent). After stirring for 1-20 h the solvent is concentrated under reduced pressure and the residue is dissolved in methanol. The resulting solution is applied to an SCX cartridge and then the cartridge is washed with MeOH. The neutral amine is then eluted from the column with 2M $NH_3$ in MeOH and then concentrated under reduced pressure. The resultant material is dissolved in methanol or ether, HCl (slight excess of a 1N solution in ether or dioxane) is added, and the mixture is concentrated under reduced pressure or filtered to provide the product. If necessary, the product can be purified, either before or after HCl salt formation, by either normal or reverse phase chromatography.

General Purification Methods

Purification Method A:

The crude product is purified by preparative chromatography on an ISCO RediSep C18 (13 g) column at 22° C. and a flow of 30 mL/min. The column is eluted with isocratic acetonitrile/0.1% aq HCl (10/90, v/v) for 1-5 min followed by a linear gradient of acetonitrile/0.1% aq HCl (10/90 through 90/10, v/v) over 20 min. The desired fractions containing purified product are then concentrated under reduced pressure.

Purification Method B:

The product is purified by preparative chromatography on an ISCO RediSep C18 (13 g) column at 22° C. and a flow of 30 mL/min. The column is eluted with isocratic 0.1% aq HCl for 1-5 min, followed by a linear gradient of acetonitrile/0.1% aq HCl (0/100 through 90/10, v/v) over 20 min. The desired fractions containing purified product are then combined and concentrated under reduced pressure.

Purification Method C:

The product is purified by preparative chromatography on an ISCO RediSep silica cartridge (330 g) column at 22° C., using a flow rate of 100 mL/min, eluting with an isocratic mixture of heptane/tetrahydrofuran/dichloromethane (70:15:15, v/v/v). The desired fractions containing purified product are then combined and concentrated under reduced pressure.

Purification Method D:

The product is purified by preparative chromatography on an ISCO RediSep silica cartridge (12 g or 40 g) column at 22° C. and a flow of 30-40 mL/min, eluting with dichloromethane for 1-5 min followed by a linear gradient of dichloromethane/2M $NH_3$ in methanol (100/0 through 87/13, v/v) over 20 min. Isocratic elution is then continued with dichloromethane/2M $NH_3$ in methanol (87/13 v/v ratio). The desired fractions containing purified product are then combined and concentrated under reduced pressure.

Purification Method E:

The crude product is purified by preparative chromatography on an ISCO RediSep silica cartridge (12 g or 40 g) column at 22° C. and a flow of 30-40 mL/min, eluting with a linear gradient of ethyl acetate/hexanes (increasing polarity) over 25 min. The desired fractions containing purified product are then combined and concentrated under reduced pressure.

Preparation of Common Intermediates:

Intermediate 1

(R,R)-1-Oxiranyl-2-phenylethylcarbamic acid, tert-butyl ester

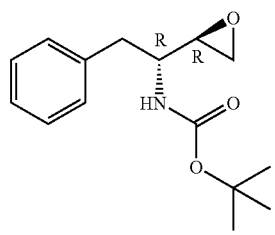

Step A:

(R)-Dimethylsufoxonium 2-oxo-3-(tert-butoxycarbonylamino)-4-phenylbutylide

To a stirring suspension of trimethylsulfoxonium iodide (34.2 g, 156 mmol) in anhydrous THF (200 mL) under an atmosphere of nitrogen, is added potassium tert-butoxide (1M solution in anhydrous THF, 163 mL, 163 mmol), and the solution is heated to reflux. After 3 h, the mixture is cooled to 0° C., and a solution of solution (R)—N-Boc-phenylalanine 4-nitrophenyl ester (20.0 g, 52 mmol) in THF (100 mL) is added dropwise, maintaining the temperature at 0° C. with an ice/water bath. After 2 h, the mixture is diluted with water and extracted twice with ethyl acetate. The combined organic layers are washed with brine (2×), dried over $Na_2SO_4$ and concentrated under reduced pressure to afford a yellow solid which is triturated in cold ethyl acetate and collected by filtration to yield a pale yellow solid (15.71 g, 46 mmol) which is used without further purification.

$^1$HNMR mass spectrum (m/e): 340 (M+1), 284 (M-C4H8+1), 240 (M-C5H8O2+1)

Step B:

(R)-1-Benzyl-3-chloro-2-oxopropylcarbamic acid tert-butyl ester

To a stirred suspension of (R)-dimethylsufoxonium 2-oxo-3-(tert-butoxycarbonylamino)-4-phenylbutylide (15.71 g, 46 mmol) and LiCl (3.72 g, 51 mmol) in anhydrous THF (250 mL) at 0° C. is added (rapidly dropwise) methanesulfonyl chloride (3.30 mL, 51 mmol). The reaction mixture is slowly heated to reflux and after stirring under a nitrogen atmosphere for an additional 2 h, the mixture is cooled, diluted with water and extracted (2×) with 2:1 heptane:ethyl acetate. The combined organic layers are washed with saturated $NaHCO_3$ (aq), water, brine, then dried over $Na_2SO_4$ and concentrated under reduced pressure to afford a pale yellow solid. Recrystallization from 5:1 heptane/ethyl acetate yields a white solid (9.91 g, 33 mmol).

$^1$HNMR mass spectrum (m/e): 320 (M+Na), 198 (M-C5H8O2+1)

Step C:

(R,R) 1-Benzyl-3-chloro-2-hydroxypropylcarbamic acid tert-butyl ester

To a stirred solution of (R)-1-Benzyl-3-chloro-2-oxopropylcarbamic acid tert-butyl ester (8.0 g, 27 mmol) in THF/water (200 mL, 9/1, v/v) at 0° C. is added NaBH$_4$ (1.23 g, 32 mmol). After 30 min the mixture is concentrated under reduced pressure and the residue is suspended in a mixture of water and ethyl acetate (1:1, v/v). This mixture is cooled to 0° C. and the pH is adjusted to ~2 by the slow addition of 2M NaHSO$_4$. The phases are separated and the organic layer is washed with water and brine, dried over Na$_2$SO$_4$ and concentrated under reduced pressure to afford a white solid as a mixture of diastereomers (7.92 g, 27 mmol, ~5:2 R,R:R,S), which is purified using General Purification Procedure C to afford the title compound as a white solid (4.45 g, 15 mmol).
$^1$HNMR
mass spectrum (m/e): 322 (M+Na), 200 (M-C5H8O2+1)

Step D:

(R,R) 1-Oxiranyl-2-phenylethylcarbamic acid tert-butyl ester

To a stirred solution of (R,R)-1-benzyl-3-chloro-2-hydroxypropylcarbamic acid tert-butyl ester (4.45 g, 15 mmol) in ethanol (125 mL) at 0° C. is added KOH (0.5M in ethanol, 36 ml, 18 mmol). After stirring for 20 min, the mixture is concentrated under reduced pressure and the residue is dissolved in ethyl acetate, washed with saturated ammonium chloride (aq), water and then brine, dried over Na$_2$SO$_4$ and concentrated under reduced pressure. The resulting white solid is purified using General Purification Procedure E to afford the title compound as a white solid (2.7 g, 10.4 mmol).
$^1$HNMR
mass spectrum (m/e): 264 (M+1)

Intermediate 2

(R,R)-[2-(2,5-Difluoro-phenyl)-1-oxiranyl-ethyl]-carbamic acid tert-butyl ester

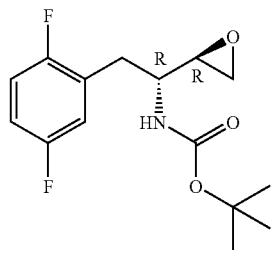

Step A:

2-tert-Butoxycarbonylamino-3-(2,5-difluorophenyl)-acrylic acid methyl ester

To a suspension of N-tert-butoxycarbonyl-phosphonoglycine trimethyl ester (12.26 g, 41 mmol) in anhydrous dichloromethane (70 mL) at 0° C. is dropwise added a solution of DBU (6.34 mL, 42 mmol, 1:1 v/v in dichloromethane) and stirred for 2 h. A solution of 2,5-difluorobenzaldehyde (5.48 g, 39 mmol) in anhydrous dichloromethane (10 mL) is then added at 0° C. and stirring continued for 3 h. The reaction mixture is then poured into a 0° C. solution of 1M NaHSO$_4$ (aq) and partitioned, and the organic layer is washed with water and brine, dried over Na$_2$SO$_4$ and concentrated under reduced pressure. The resulting brown oil is purified using General Purification Procedure E to afford the title compound as a white crystalline solid (6.5 g, 22 mmol)
$^1$HNMR Step B:

(R)-2-tert-Butoxycarbonylamino-3-(2,5-difluorophenyl)-propionic acid methyl ester To a solution of 2-tert-butoxycarbonylamino-3-(2,5-difluorophenyl)-acrylic acid methyl ester (4.9 g, 15.7 mmol) in methanol (49 mL) is added (−)-1,2-bis((2R,5R)-2,5-diethylphospholano)benzene(cyclooctadiene)rhodium(I) tetrafluoroborate (113 mg, 0.15 mmol), and is shaken for 20 h under an atmosphere of H$_2$ at 75 psi. The suspension is filtered through Celite to remove catalyst and concentrated under reduced pressure to afford a light yellow solid. The solid is triturated in cold methanol to afford the title compound as a white solid (4.75 g, 15.4 mmol)
$^1$HNMR Step C:

(R)-2-tert-Butoxycarbonylamino-3-(2,5-difluorophenyl)-propionic acid

Using general procedure 6, (R)-2-tert-butoxycarbonylamino-3-(2,5-difluorophenyl)-propionic acid methyl ester gives the title compound.
$^1$HNMR
mass spectrum (m/e): 324 (M+Na), 268 (M-C4H8+1)

Step D:

(R)-2-tert-Butoxycarbonylamino-3-(2,5-difluorophenyl)-propionic acid 4-nitrophenyl ester To a solution of (R)-2-tert-butoxycarbonylamino-3-(2,5-difluorophenyl)-propionic acid (8.0 g, 27 mmol) in anhydrous dichloromethane (200 mL) at 0° C. is added N-ethyl-N',N'-dimethylaminoethyl carbodiimide (5.09 g, 27 mmol), followed by 4-nitrophenol (4.4 g, 32 mmol). After stirring for 30 min, the solution is washed sequentially with saturated NaHCO3 (aq), water, 1.0 M citric acid (aq), water and brine, then dried over Na$_2$SO$_4$ and concentrated under reduced pressure to afford the title compound as a slightly red solid (8.11 g, 19 mmol), contaminated with residual 4-nitrophenol, which may be used without purification.
$^1$HNMR Step E:

(R)-Dimethylsufoxonium 2-oxo-3-(tert-butoxycarbonylamino)-4-(2,5-difluorophenyl)butylide To a suspension of trimethylsulfoxonium iodide (12.7 g, 58 mmol) in anhydrous THF (100 mL) is added an anhydrous solution of 1M potassium tert-butoxide in T-F (62 mL, 62 mmol) and stirred for 3 h at 67° C. under an atmosphere of nitrogen in a 3-neck flask fitted with a reflux condenser. After cooling to 0° C., a THF (50 mL) solution of (R)—N-tert-butoxycarbonyl-2,5-difluorophenylalanine 4-nitrophenyl ester (8.11 g, 19 mmol) is added dropwise, maintaining the temperature at 0° C. with an ice/water bath. After 2 h, the reaction mixture is quenched with water and extracted twice with ethyl acetate. The combined organic layers are washed with brine (2×), dried over Na$_2$SO$_4$ and concentrated under reduced pressure to afford a yellow solid which may be used without further purification (6.0 g, 16 mol)

$^1$HNMR

Step F:

(R)-1-(2,5-Difluorophenylmethyl)-3-chloro-2-oxo-propylcarbamic acid tert-butyl ester To a stirred suspension of (R)-dimethylsufoxonium 2-oxo-3-(tert-butoxycarbonylamino)-4-(2,5-difluorophenyl)butylide (6.0 g, 16 mmol) and LiCl (1.34 g, 18 mmol) in anhydrous THF (100 mL) at 0° C. is added rapidly dropwise methanesulfonyl chloride (1.14 mL, 18 mmol). The temperature is slowly raised to 67° C. and stirring continues under a nitrogen atmosphere at reflux for 2 h. The reaction mixture is then cooled to 0° C., quenched with water and extracted (2×) with 2:1 heptane:ethyl acetate. The combined organic layers are washed with saturated NaHCO$_3$ (aq), water, and brine, then dried over Na$_2$SO$_4$ and concentrated under reduced pressure to afford a pale yellow solid. The material is purified using General Purification Procedure E to afford the title compound as a white solid (3.56 g, 11 mmol).

$^1$HNMR mass spectrum (m/e): 356 (M+Na), 278 (M-C4H8+1), 234 (M-C5H8O2+1)

Step G:

(R,R)-1-(2,5-Difluorophenylmethyl)-3-chloro-2-hydroxypropylcarbamic acid tert-butyl ester To a stirred solution of (R)-1-(2,5-difluorophenylmethyl)-3-chloro-2-oxopropylcarbamic acid tert-butyl ester (3.56 g, 11 mmol) in a solution of 9:1 THF:water (150 mL) at 0° C. is added NaBH$_4$ (0.49 g, 13 mmol, 1.2 eq) and stirred for 5 min. The reaction mixture is concentrated under reduced pressure to a white solid which is suspended in a mixture of water and ethyl acetate. This biphasic mixture is cooled to 0° C. and quenched slowly with 2M NaHSO$_4$ until pH~2 and the layers rapidly separated. The organic layer is washed with water and brine, dried over Na$_2$SO$_4$ and concentrated under reduced pressure to afford a white solid as a mixture of diastereomers (3.5 g, 13 mmol, ~5:2 R,R:R,S). The crude material was purified using General Purification Procedure C to afford the title compound as a single diastereomer of a white solid (2.2 g, 6.6 mmol).

$^1$HNMR mass spectrum (m/e): 358 (M+Na), 280 (M-C4H8+1), 236 (M-C5H8O2+1)

Step H:

(R,R)-1-Oxiranyl-2-(2,5-difluorophenyl)ethylcarbamic acid tert-butyl ester

To a stirred solution of (R,R)-1-(2,5-difluorophenylmethyl)-3-chloro-2-hydroxypropylcarbamic acid tert-butyl ester (2.2 g, 6.6 mmol) in ethanol (100 mL) at 0° C. is added a 0.5M solution of KOH in ethanol (15.7 mL, 7.9 mmol, 1.2 eq) and is stirred for 90 min. The reaction mixture is concentrated under reduced pressure and the residue is redissolved in ethyl acetate. The solution is washed sequentially with saturated ammonium chloride (aq), water and brine, then dried over Na$_2$SO$_4$ and concentrated under reduced pressure to afford the title compound as a white solid (1.86 g, 6.2 mmol).

$^1$HNMR mass spectrum (m/e): 300 (M+1), 244 (M-C4H8+1), 200 (M-C5H8O2+1), 322 (M+Na)

Preparation of DPIV Inhibitors:

Example 1

(2S,3R)-3-Amino-4-phenyl-1-[1,2,3]triazol-1-yl-butan-2-ol Hydrochloride

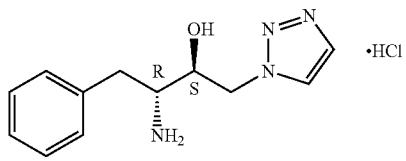

Step A:

[(1R,2S)-1-Benzyl-2-hydroxy-3-[1,2,3]triazol-1-yl-propyl]-carbamic acid tert-butyl ester Using general procedure 4 and purification method E with [(1R)-1-{(2R)-oxiran-2-yl}-2-phenyl-ethyl]carbamic acid tert-butylester (0.15 g, 0.57 mmol) and 1,2,3-triazole (0.037 mL, 0.63 mmol) gives the title compound.

$^1$HNMR mass spectrum (m/e): 333 (M+1), 355 (M+Na)

Step B:

(2S,3R)-3-Amino-4-phenyl-1-[1,2,3]triazol-1-yl-butan-2-ol Hydrochloride

Using general procedure 10 and purification method D with [(1R,2S)-1-benzyl-2-hydroxy-3-[1,2,3]triazol-1-yl-propyl]-carbamic acid tert-butyl ester (0.099 g, 0.30 mmol) gives the title compound.

$^1$HNMR (400 MHz, DMSO) δ 2.86 (dd, J=8.1, 13.9 Hz, 1H), 3.05 (dd, J=5.6, 14.2 Hz, 1H), 3.43 (br, 1H), 4.12-4.17 (m, 1H), 4.35 (dd, J=9.0, 14.0 Hz, 1H), 4.63 (dd, J=4.6, 13.8 Hz, 1H), 6.0 (br, 1H), 7.24-7.39 (m, 5H), 7.73 (s, 1H), 8.04 (s, 1H), 8.07 (br, 3H)

mass spectrum (m/e): 233 (M+1), 255 (M+Na)

Example 2

(2S,3R)-3-Amino-4-phenyl-1-[1,2,3]triazol-2-yl-butan-2-ol Hydrochloride

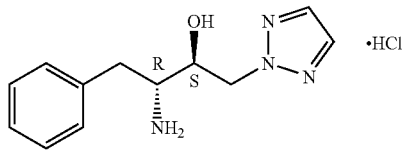

Step A:

[(1R,2S)-1-Benzyl-2-hydroxy-3-[1,2,3]triazol-2-yl-propyl]-carbamic acid tert-butyl ester Using general procedure 4 and purification method E with [(1R)-1-{(2R)-oxiran-2-yl}-2-phenyl-ethyl]carbamic acid tert-butylester (0.15 g, 0.57 mmol) and 1,2,3-triazole (0.037 mL, 0.63 mmol) gives the title compound.

¹HNMR mass spectrum (m/e): 277 (M-C4H8+1), 355 (M+Na)

Step B:

(2S,3R)-3-Amino-4-phenyl-1-[1,2,3]triazol-2-yl-butan-2-ol Hydrochloride

Using general procedure 10 and purification method B (with a solvent gradient of 5/95 to 50/50 in this case) [(1R,2S)-1-benzyl-2-hydroxy-3-[1,2,3]triazol-2-yl-propyl]-carbamic acid tert-butyl ester (0.069 g, 0.21 mmol) gives the title compound.

¹HNMR (400 MHz, DMSO) δ 2.85 (dd, J=8.7, 14.6 Hz, 1H), 3.08 (dd, J=5.9, 14.4 Hz, 1H), 3.37 (br, 1H), 4.29-4.36 (m, 1H), 4.43 (dd, J=8.7, 13.9 Hz, 1H), 4.59 (dd, J=4.59, 13.7 Hz, 1H), 5.89 (d, J=6.61 Hz, 1H), 7.25-7.36 (m, 5H), 7.82 (s, 2H), 7.99 (br, 3H)

mass spectrum (m/e): 233 (M+1)

Example 3

(2S,3R)-3-Amino-4-phenyl-1-[1,2,4]triazol-1-yl-butan-2-ol Hydrochloride

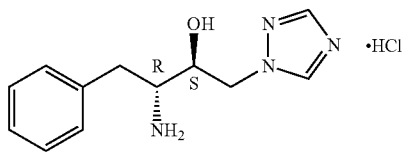

Step A:

[(1R,2S)-1-Benzyl-2-hydroxy-3-[1,2,4]triazol-1-yl-propyl]-carbamic acid tert-butyl ester Using general procedure 4 with [(1R)-1-{(2R)-oxiran-2-yl}-2-phenyl-ethyl]carbamic acid tert-butylester (0.125 g, 0.47 mmol) and 1,2,4-triazole (0.036 g, 0.52 mmol) gives the title compound (recrystallized from ethyl acetate).

¹HNMR mass spectrum (m/e): 277 (M-C4H8+1), 355 (M+Na)

Step B:

(2S,3R)-3-Amino-4-phenyl-1-[1,2,4]triazol-1-yl-butan-2-ol Hydrochloride

Using general procedure 10 and purification method D with [(1R,2S)-1-benzyl-2-hydroxy-3-[1,2,4]triazol-1-yl-propyl]-carbamic acid tert-butyl ester (0.080 g, 0.24 mmol) gives the title compound.

¹HNMR (400 MHz, DMSO) δ 2.85 (dd, J=8.3, 14.1 Hz, 1H), 3.03 (dd, J=5.8, 14.1 Hz, 1H), 3.40-3.48 (m, 1H), 4.10-4.16 (m, 1H), 4.20 (dd, J=8.8, 14.3 Hz, 1H), 4.35 (dd, J=3.8, 14.0 Hz, 1H), 5.89 (br, 1H), 7.24-7.39 (m, 5H), 8.02 (s, 1H), 8.05 (br, 3H), 8.56 (s, 1H)

mass spectrum (m/e): 233 (M+1)

Example 4

(2S,3R)-3-Amino-4-phenyl-1-([3R,S]-3-phenyl-pyrrolidin-1-yl)-butan-2-ol Dihydrochloride

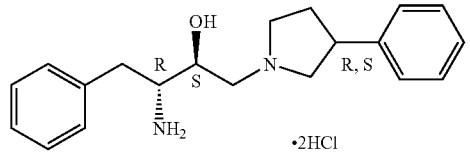

Step A:

[(1R,2S)-1-Benzyl-2-hydroxy-3-([3R,S]-3-phenyl-pyrrolidin-1-yl)-propyl]-carbamic acid tert-butyl ester Using general procedure 1 and purification method E with [(1R)-1-{(2R)-oxiran-2-yl}-2-phenyl-ethyl]carbamic acid tert-butylester (0.15 g, 0.57 mmol) and (3R,S)-3-phenyl-pyrrolidine (0.10 mL, 0.68 mmol) gives the title compound.

¹H NMR mass spectrum (m/e): 411 (M+1), 355 (M-C4H8+1)

Step B:

(2S,3R)-3-Amino-4-phenyl-1-([3R,S]-3-phenyl-pyrrolidin-1-yl)-butan-2-ol Dihydrochloride Using general procedure 9 and purification method A with [(1R,2S)-1-benzyl-2-hydroxy-3-([3R,S]-3-phenyl-pyrrolidin-1-yl)-propyl]-carbamic acid tert-butyl ester (0.076 g, 0.19 mmol) gives the title compound.

¹H NMR (400 MHz, CDCl₃, as free base) δ 1.38 (br, 2H), 1.88-1.96 (m, 1H), 2.32-2.38 (m, 1H), 2.49-2.61 (m, 3H), 2.71-2.81 (m, 2H), 2.86-3.01 (m, 3H), 3.14-3.20 (m, 1H), 3.36-3.43 (m, 1H), 3.60-3.67 (m, 1H), 7.19-7.33 (m, 10H)

mass spectrum (m/e): 311 (M+1)

Example 5

(2S,3R)-3-Amino-4-phenyl-1-(4-phenyl-piperidin-1-yl)-butan-2-ol Dihydrochloride

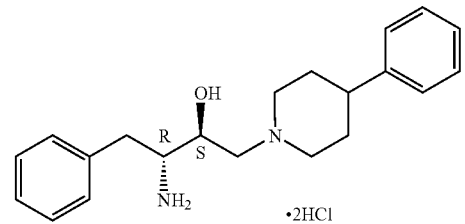

Step A:

[(1R,2S)-1-Benzyl-2-hydroxy-3-(4-phenyl-piperidin-1-yl)-propyl]-carbamic acid tert-butyl ester Using general procedure 1 and purification method E with [(1R)-1-{(2R)-oxiran-2-yl}-2-phenyl-ethyl]carbamic acid tert-butylester (0.10 g, 0.38 mmol) and 4-phenyl-piperidine (0.122 g, 0.76 mmol) gives the title compound.
¹HNMR
mass spectrum (m/e): 425 (M+1), 369 (M-C4H8+1)

Step B:

(2S,3R)-3-Amino-4-phenyl-1-(4-phenyl-piperidin-1-yl)-butan-2-ol Dihydrochloride

Using general procedure 9 and purification method A with [(1R,2S)-1-benzyl-2-hydroxy-3-(4-phenyl-piperidin-1-yl)-propyl]-carbamic acid tert-butyl ester (0.119 g, 0.28 mmol) gives the title compound.
¹H NMR (400 MHz, CDCl₃, as free base) δ 1.35 (br, 2H), 1.69-1.90 (m, 4H), 2.03-2.09 (m, 1H), 2.43-2.65 (m, 5H), 2.94-3.01 (m, 2H), 3.11-3.19 (m, 2H), 3.63-3.68 (m, 1H), 7.19-7.29 (m, 6H), 7.30-7.34 (m, 4H)
mass spectrum (m/e): 325 (M+1)

Example 6

(2S,3R)-3-Amino-4-phenyl-1-([3R,S]-3-phenyl-piperidin-1-yl)-butan-2-ol Dihydrochloride

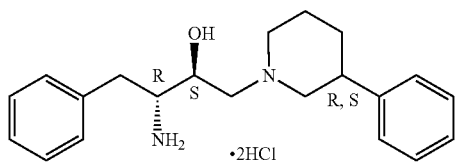

Step A:

[(1R,2S)-1-Benzyl-2-hydroxy-3-([3R,S]-3-phenyl-piperidin-1-yl)-propyl]-carbamic acid tert-butyl ester Using general procedure 1 and purification method E with [(1R)-1-{(2R)-oxiran-2-yl}-2-phenyl-ethyl]carbamic acid tert-butylester (0.20 g, 0.67 mmol) and (3R,S)-3-phenyl-piperidine (0.50 g, 3.1 mmol) gives the title compound.
¹H NMR
mass spectrum (m/e): 425 (M+1), 369 (M-C4H8+1)

Step B:

(2S,3R)-3-Amino-4-phenyl-1-([3R,S]-3-phenyl-piperidin-1-yl)-butan-2-ol Dihydrochloride Using general procedure 9 and purification method D with [(1R,2S)-1-benzyl-2-hydroxy-3-([3R,S]-3-phenyl-piperidin-1-yl)-propyl]-carbamic acid tert-butyl ester (0.131 g, 0.31 mmol) gives the title compound.
¹H NMR (400 MHz, CDCl₃, as free base) δ 1.44-1.56 (m, 2H), 1.63-1.85 (m, 3H), 1.92-2.10 (m, 3H), 2.34-2.69 (m, 4H), 2.77-3.01 (m, 3H), 3.11-3.16 (m, 2H), 3.66-3.68 (m, 1H), 7.19-7.24 (m, 6H), 7.27-7.33 (m, 4H)
mass spectrum (m/e): 325 (M+1)

Example 7

(2S)-1-[(2S,3R)-3-Amino-2-hydroxy-4-phenyl-butyl]-pyrrolidine-2-carboxylic acid amide Dihydrochloride

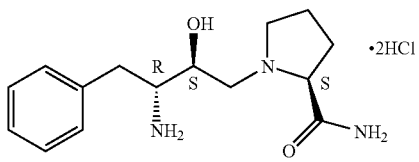

Step A:

[(1R,2S)-1-Benzyl-3-([2S]-2-carbamoyl-pyrrolidin-1-yl)-2-hydroxy-propyl]-carbamic acid tert-butyl ester Using general procedure 1 and purification method D with [(1R)-1-{(2R)-oxiran-2-yl}-2-phenyl-ethyl]carbamic acid tert-butylester (0.10 g, 0.38 mmol) and (S)-proline amide (0.114 g, 0.57 mmol) gives the title compound.
mass spectrum (m/e): 378 (M+1), 322 (M-C4H8+1)

Step B:

(2S)-1-[(2S,3R)-3-Amino-2-hydroxy-4-phenyl-butyl]-pyrrolidine-2-carboxylic acid amide Dihydrochloride Using general procedure 9 and purification method A with [(1R,2S)-1-benzyl-3-([2S]-2-carbamoyl-pyrrolidin-1-yl)-2-hydroxy-propyl]-carbamic acid tert-butyl ester (0.10 g, 0.23 mmol) gives the title compound.
¹H NMR (400 MHz, CDCl₃, as free base) δ 1.2 (br, 2H), 1.83-1.88 (m, 2H), 1.93-1.97 (m, 1H), 2.19-2.26 (m, 1H), 2.30-2.36 (m, 1H), 2.49 (dd, J=10.5, 13.6 Hz, 1H), 2.60 (dd, J=2.2, 13.3 Hz, 1H), 2.82-2.88 (m, 2H), 3.09-3.19 (m, 2H), 3.26-3.31 (m, 1H), 3.49 (s, 1H), 3.71-3.75 (m, 1H), 5.38 (br s, 1H), 7.18-7.26 (m, 3H), 7.29-7.34 (m, 2H), 7.45 (br s, 1H)
mass spectrum (m/e): 278 (M+1)

Example 8

(2S,3R)-3-Amino-1-benzotriazol-1-yl-4-phenyl-butan-2-ol Hydrochloride

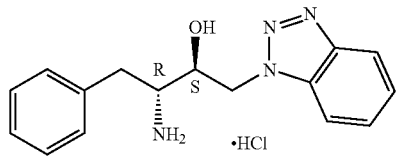

Step A:

[(1R,2S)-3-Benzotriazol-1-yl-1-benzyl-2-hydroxy-propyl]-carbamic acid tert-butyl ester Using general procedure 4 and purification method E with [(1R)-1-{(2R)-oxiran-2-yl}-2-phenyl-ethyl]carbamic acid tert-butylester (0.25 g, 0.95 mmol) and 1,2,3-benzotriazole (0.136 g, 1.14 mmol) gives the title compound.

¹HNMR mass spectrum (m/e): 327 (M-C4H8+1), 405 (M+Na)

Step B:

(2S,3R)-3-Amino-1-benzotriazol-1-yl-4-phenyl-butan-2-ol Hydrochloride

Using general procedure 10, [(1R,2S)-3-benzotriazol-1-yl-1-benzyl-2-hydroxy-propyl]-carbamic acid tert-butyl ester (0.168 g, 0.44 mmol) gives the title compound.

¹HNMR (400 MHz, DMSO) δ 2.96 (dd, J=8.1, 14.2 Hz, 1H), 3.17 (dd, J=6.2, 14.2 Hz, 1H), 3.57-3.66 (m, 1H), 4.26-4.32 (m, 1H), 4.68 (dd, J=9.5, 14.1 Hz, 1H), 4.88 (dd, J=3.6, 14.5 Hz, 1H), 7.26-7.42 (m, 6H), 7.54 (t, J=7.9 Hz, 1H), 7.80 (d, J=8.0 Hz, 1H), 8.03 (d, J=8.0 Hz, 1H), 8.11 (br, 3H)

mass spectrum (m/e): 283 (M+1), 305 (M+Na)

Example 9

(2S,3R)-3-Amino-1-benzotriazol-2-yl-4-phenyl-butan-2-ol Hydrochloride

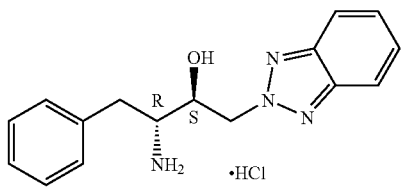

Step A:

[(1R,2S)-3-Benzotriazol-2-yl-1-benzyl-2-hydroxy-propyl]-carbamic acid tert-butyl ester Using general procedure 4 and purification method E (elute with isocratic 20% ethyl acetate/hexanes in this case) with [(1R)-1-{(2R)-oxiran-2-yl}-2-phenyl-ethyl]carbamic acid tert-butylester (0.25 g, 0.95 mmol) and 1,2,3-benzotriazole (0.136 g, 1.14 mmol) gives the title compound.

¹HNMR mass spectrum (m/e): 327 (M-C4H8+1), 405 (M+Na)

Step B:

(2S,3R)-3-Amino-1-benzotriazol-2-yl-4-phenyl-butan-2-ol Hydrochloride

Using general procedure 10 and purification method D with [(1R,2S)-3-benzotriazol-2-yl-1-benzyl-2-hydroxy-propyl]-carbamic acid tert-butyl ester (0.107 g, 0.28 mmol) gives the title compound.

¹HNMR (400 MHz, DMSO) δ 2.92 (dd, J=8.2, 14.3 Hz, 1H), 3.14 (dd, J=6.0, 14.3 Hz, 1H), 3.51-3.60 (br m, 1H), 4.52-4.58 (br m, 1H), 4.70 (dd, J=9.4, 13.5 Hz, 1H), 4.93 (dd, J=4.1, 13.5 Hz, 1H), 5.9 (d, J=6.0 Hz, 1H), 7.25-7.32 (m, 1H), 7.34-7.39 (m, 4H), 7.41-7.46 (m, 2H), 7.89-7.94 (m, 2H), 8.09 (br, 3H)

mass spectrum (m/e): 283 (M+1), 305 (M+Na)

Example 10

(2S)-1-[(2S,3R)-3-Amino-2-hydroxy-4-phenyl-butyl]-pyrrolidine-2-carboxylic acid ethylamide Dihydrochloride

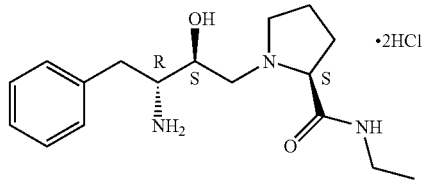

Step A:

[(1R,2S)-1-Benzyl-3-([2S]-2-ethylcarbamoyl-pyrrolidin-1-yl)-2-hydroxy-propyl]-carbamic acid tert-butyl ester Using general procedure 1 and purification method D with [(1R)-1-{(2R)-oxiran-2-yl}-2-phenyl-ethyl]carbamic acid tert-butylester (0.10 g, 0.38 mmol) and (S)-proline ethyl amide (0.108 g, 0.76 mmol) gives the title compound.

¹HNMR mass spectrum (m/e): 406 (M+1), 350 (M-C4H8+1), 306 (M-C5H8O2+1)

Step B:

(2S)-1-[(2S,3R)-3-Amino-2-hydroxy-4-phenyl-butyl]-pyrrolidine-2-carboxylic acid ethylamide Dihydrochloride Using general procedure 9 with [(1R,2S)-1-benzyl-3-([2S]-2-ethylcarbamoyl-pyrrolidin-1-yl)-2-hydroxy-propyl]-carbamic acid tert-butyl ester (0.15 g, 0.38 mmol) gives the title compound.

¹H NMR (400 MHz, CDCl3, as free base) δ 1.13 (t, J=7.1 Hz, 3H), 1.76-1.89 (m, 5H), 2.17-2.22 (m, 1H), 2.27-2.33 (m, 1H), 2.48 (dd, J=10.1, 13.7 Hz, 1H), 2.54 (dd, J=2.0, 12.4 Hz, 1H), 2.76-2.84 (m, 2H) 3.06-3.15 (m, 2H), 3.18-3.38 (m, 3H), 3.67-3.73 (m, 1H), 7.17-7.24 (m, 3H), 7.30 (t, J=7.5 Hz, 2H), 7.61 (br t, 1H)

mass spectrum (m/e): 306 (M+1)

Example 11

(2S,3R)-3-Amino-1-indazol-1-yl-4-phenyl-butan-2-ol Hydrochloride

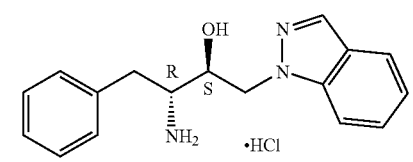

Step A:

[(1R,2S)-1-Benzyl-2-hydroxy-3-indazol-1-yl-propyl]-carbamic acid tert-butyl ester Using general procedure 4 and purification method E with [(1R)-1-{(2R)-oxiran-2-yl}-2-phenyl-ethyl]carbamic acid tert-butylester (0.25 g, 0.95 mmol) and indazole (0.56 g, 4.74 mmol) gives the title compound.
¹HNMR
mass spectrum (m/e): 382 (M+1), 405 (M+Na)

Step B:

(2S,3R)-3-Amino-1-indazol-1-yl-4-phenyl-butan-2-ol Hydrochloride

Using general procedure 10 with [(1R,2S)-1-benzyl-2-hydroxy-3-indazol-1-yl-propyl]-carbamic acid tert-butyl ester (0.14 g, 0.37 mmol) gives the title compound.
¹HNMR (400 MHz, DMSO) δ 2.90 (dd, J=8.5, 14.4 Hz, 1H), 3.17 (dd, J=5.5, 14.4 Hz, 1H), 3.34-3.42 (m, 1H, partially obscured by H2O peak), 4.24-4.30 (m, 1H), 4.43 (dd, J=7.8, 14.1 Hz, 1H), 4.51 (dd, J=5.3, 14.5, Hz, 1H), 5.80 (br, 1H), 7.13 (t, J=7.6 Hz, 1H), 7.27-7.40 (m, 6H), 7.62 (d, J=8.3 Hz, 1H), 7.75 (d, J=8.3 Hz, 1H), 8.0 (br, 3H), 8.11 (s, 1H)
mass spectrum (m/e): 282 (M+1), 305 (M+Na)

Example 12

(2S,3R)-3-Amino-1-indazol-2-yl-4-phenyl-butan-2-ol Hydrochloride

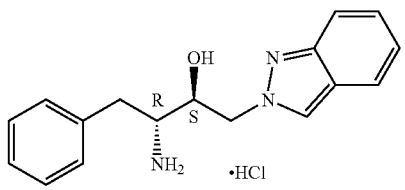

Step A:

[(1R,2S)-1-Benzyl-2-hydroxy-3-indazol-2-yl-propyl]-carbamic acid tert-butyl ester Using general procedure 4 and purification method E with [(1R)-1-{(2R)-oxiran-2-yl}-2-phenyl-ethyl]carbamic acid tert-butylester (0.25 g, 0.95 mmol) and indazole (0.56 g, 4.74 mmol) gives the title compound.
¹HNMR
mass spectrum (m/e): 382 (M+1), 405 (M+Na)

Step B:

(2S,3R)-3-Amino-1-indazol-2-yl-4-phenyl-butan-2-ol Hydrochloride

Using general procedure 10 with [(1R,2S)-1-benzyl-2-hydroxy-3-indazol-2-yl-propyl]-carbamic acid tert-butyl ester (0.122 g, 0.32 mmol) gives the title compound.
¹HNMR (400 MHz, DMSO) δ 2.77 (dd, J=8.5, 13.9 Hz, 1H), 3.07 (dd, J=5.1, 14.1 Hz, 1H), 3.20-3.26 (m, 1H), 4.17-4.24 (m, 1H), 4.41 (dd, J=8.1, 13.5 Hz, 1H), 4.63 (dd, J=4.4, 9.3 Hz, 1H), 5.72-5.77 (m, 1H), 6.92 (br, 3H), 7.02 (t, J=7.2 Hz, 1H), 7.20-7.26 (m, 2H), 7.30-7.32 (m, 4H), 7.57 (d, J=8.6 Hz, 1H), 7.70 (d, J=8.6 Hz, 1H), 8.3 (s, 1H)
mass spectrum (m/e): 282 (M+1), 305 (M+Na)

Example 13

(2S,3R)-3-Amino-4-phenyl-1-pyrazol-1-yl-butan-2-ol Hydrochloride

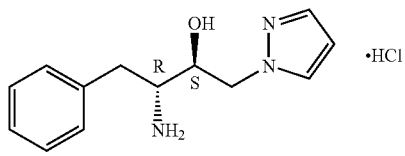

Step A:

[(1R,2S)-1-Benzyl-2-hydroxy-3-pyrazol-1-yl-propyl]-carbamic acid tert-butyl ester Using general procedure 3, [(1R)-1-{(2R)-oxiran-2-yl}-2-phenyl-ethyl]carbamic acid tert-butylester (0.15 g, 0.59 mmol) and pyrazole (0.194 g, 2.85 mmol) gives the title compound.
In this example, the product taken to step B without purification or characterization.

Step B:

(2S,3R)-3-Amino-4-phenyl-1-pyrazol-1-yl-butan-2-ol Hydrochloride

Using general procedure 10 and purification method B (using a gradient of 5/95-30/70 in this case), followed by purification method D, with [(1R,2S)-1-benzyl-2-hydroxy-3-pyrazol-1-yl-propyl]-carbamic acid tert-butyl ester (0.305 g, 0.92 mmol) gives the title compound.
¹HNMR (400 MHz, DMSO) δ 2.82 (dd, J=8.4, 14.4 Hz, 1H), 3.04 (dd, J=5.4, 14.4 Hz, 1H), 3.22-3.30 (m, 1H), 4.09-4.19 (m, 2H, partially obscured by br H2O peak), 4.24-4.35 (m, 1H), 6.25 (t, J=1.8 Hz, 1H), 7.24-7.35 (m, 5H), 7.48 (d, J=1.7, 1H), 7.65 (d, J=2.1 Hz, 1H), 8.0 (br, 3H)
mass spectrum (m/e): 232 (M+1), 254 (M+Na)

Example 14

(2S,3R)-3-Amino-1-imidazol-1-yl-4-phenyl-butan-2-ol Hydrochloride

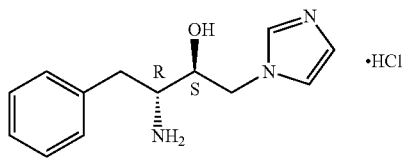

Step A:

[(1R,2S)-1-Benzyl-2-hydroxy-3-imidazol-1-yl-propyl]-carbamic acid tert-butyl ester Using general procedure 2 and purification method D with [(1R)-1-{(2R)-oxiran-2-yl}-2-phenyl-ethyl]carbamic acid tert-butylester (0.166 g, 0.63 mmol) and imidazole (0.052 g, 0.76 mmol) gives the title compound.
mass spectrum (m/e): 332 (M+1), 354 (M+Na)

Step B:

(2S,3R)-3-Amino-1-imidazol-1-yl-4-phenyl-butan-2-ol Hydrochloride

Using general procedure 10 with [(1R,2S)-1-benzyl-2-hydroxy-3-imidazol-1-yl-propyl]-carbamic acid tert-butyl ester (0.053 g, 0.16 mmol) gives the title compound (which can be washed with pentane).

¹HNMR (400 MHz, DMSO) δ 2.83 (dd, J=8.1, 14.1 Hz, 1H), 2.99 (dd, J=5.9, 14.7 Hz, 1H), 3.34-3.40 (m, 1H, partially obscured by H2O peak), 3.94-3.99 (m, 2H), 4.22-4.28 (m, 1H), 5.95 (d, J=5.5 Hz, 1H), 7.09 (s, 1H), 7.24-7.29 (m, 2H), 7.31-7.34 (m, 4H), 7.94 (s, 1H), 8.0 (br, 3H)

mass spectrum (m/e): 232 (M+1)

Example 15

(2S,3R)-3-Amino-1-benzimidazol-1-yl-4-phenyl-butan-2-ol Hydrochloride

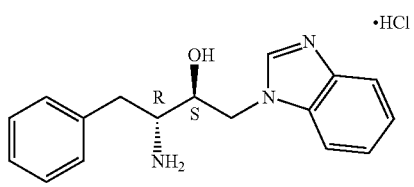

Step A:

[(1R,2S)-3-Benzimidazol-1-yl-1-benzyl-2-hydroxy-propyl]-carbamic acid tert-butyl ester Using general procedure 2 and purification method D with [(1R)-1-{(2R)-oxiran-2-yl}-2-phenyl-ethyl]carbamic acid tert-butylester (0.125 g, 0.48 mmol) and benzimidazole (0.067 g, 0.57 mmol) gives the title compound.

¹HNMR mass spectrum (m/e): 382 (M+1)

Step B:

(2S,3R)-3-Amino-1-benzimidazol-1-yl-4-phenyl-butan-2-ol Hydrochloride

Using general procedure 10 with [(1R,2S)-3-benzimidazol-1-yl-1-benzyl-2-hydroxy-propyl]-carbamic acid tert-butyl ester (0.033 g, 0.09 mmol) gives the title compound.

¹HNMR (400 MHz, DMSO) 62.92 (dd, J=8.2, 14.1 Hz, 1H), 3.11 (dd, J=5.6, 14.3 Hz 1H), 3.60-3.69 (m, 1H), 4.06-4.14 (m, 1H), 4.20-4.29 (m, 1H), 4.52-4.60 (m, 1H), 5.97 (d, J=6.1 Hz, 1H), 7.29-7.39 (m, 8H), 7.70-7.73 (m, 2H), 8.1 (m, 3H), 8.59 (br, 1H)

mass spectrum (m/e): 282 (M+1)

Example 16

(2S,3R)-3-Amino-1-[(2S)-2-(4-fluorophenyl)-pyrrolidin-1-yl]-4-phenyl-butan-2-ol Dihydrochloride

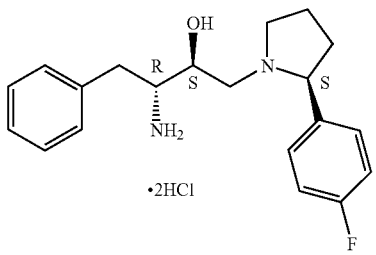

Step A:

[(1R,2S)-1-Benzyl-3-[(2S)-2-(4-fluoro-phenyl)-pyrrolidin-1-yl]-2-hydroxy-propyl)-carbamic acid tert-butyl ester Using general procedure 1 and purification method D with [(1R)-1-{(2R)-oxiran-2-yl}-2-phenyl-ethyl]carbamic acid tert-butylester (0.10 g, 0.38 mmol) and (2S)-2-(4-fluorophenyl)-pyrrolidine (0.10 g, 0.60 mmol) gives the title compound.

¹HNMR mass spectrum (m/e): 429 (M+1), 373 (M-C4H8+1)

Step B:

(2S,3R)-3-Amino-1-[(2S)-2-(4-fluorophenyl)-pyrrolidin-1-yl]-4-phenyl-butan-2-ol Dihydrochloride Using general procedure 9 and purification method D with [(1R,2S)-1-benzyl-3-[(2S)-2-(4-fluoro-phenyl)-pyrrolidin-1-yl]-2-hydroxy-propyl)-carbamic acid tert-butyl ester (0.117 g, 0.27 mmol) gives the title compound.

¹H NMR (400 MHz, CDCl₃, as free base) δ 1.32 (br, 2H), 1.69-1.77 (m, 1H), 1.83-2.04 (m, 2H), 2.14-2.22 (m, 1H), 2.25-2.31 (m, 1H), 2.34 (dd, J=3.1, 11.9 Hz, 1H), 2.42 (dd, J=9.7, 13.6 Hz, 1H), 2.62 (dd, J=10.9, 11.5 Hz, 1H), 2.89 (dd, J=4.0, 13.7 Hz, 1H), 2.88-3.00 (m, 1H), 3.38-3.44 (m, 2H), 3.56-3.61 (m, 1H), 6.99-7.05 (m, 2H), 7.15-7.21 (m, 3H), 7.25-7.31 (m, 4H)

mass spectrum (m/e): 329 (M+1)

Examples 17a and 17b

(2S,3R)-3-Amino-4-phenyl-1-([2R,S]-2-phenyl-pyrrolidin-1-yl)-butan-2-ol Dihydrochloride

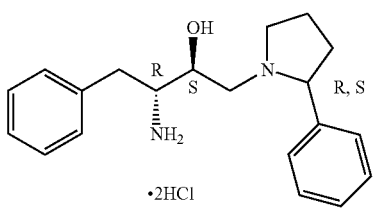

Step A:

[(1R,2S)-1-Benzyl-2-hydroxy-3-([2R,S]-2-phenyl-pyrrolidin-1-yl)-propyl]-carbamic acid tert-butyl ester Using general procedure 1 and purification method D with [(1R)-1-{(2R)-oxiran-2-yl}-2-phenyl-ethyl]carbamic acid tert-butylester (0.20 g, 0.76 mmol) and (2R,S)-2-phenyl-pyrrolidine (0.224 g, 1.5 mmol) gives the title compound.
¹H NMR
mass spectrum (m/e): 411 (M+1), 355 (M-C4H8+1)
Step B:

(2S,3R)-3-Amino-4-phenyl-1-([2R,S]-2-phenyl-pyrrolidin-1-yl)-butan-2-ol Dihydrochloride Using general procedure 9 and purification method D with [(1R,2S)-1-benzyl-2-hydroxy-3-([2R,S]-2-phenyl-pyrrolidin-1-yl)-propyl]-carbamic acid tert-butyl ester (0.236 g, 0.58 mmol) gives the title compounds.
(Example 17a: less polar isomer) RP-HPLC: RT=4.93 min [Xterra™ RP18 (4.6×150 mm), ambient temperature (~22° C.), 1.5 mL/min elution with a 5 min linear gradient of acetonitrile/0.1% aq TFA (10/90 through 90/10, v/v), followed by isocratic elution with acetonitrile/0.1% aq TFA (90/10, v/v) for 2 min]
¹H NMR (400 MHz, CDCl₃, as free base) δ 1.61 (br, 2H), 1.76-2.03 (m, 3H), 2.17-2.26 (m, 1H), 2.28-2.45 (m, 1H), 2.36-2.45 (m, 3H), 2.67 (dd, J=10.6, 11.8 Hz, 1H), 2.87 (dd, J=4.4, 13.7 Hz, 1H), 2.95-3.00 (m, 1H), 3.44-3.49 (m, 2H), 3.57-3.62 (m, 1H), 7.14-7.21 (m, 3H), 7.24-7.29 (m, 3H), 7.31-7.35 (m, 4H)
mass spectrum (m/e): 311 (M+1)

(Example 17b: more polar isomer) RP-HPLC: RT=4.85 min [Xterra™ RP18 (4.6×150 mm), ambient temperature (~22° C.), 1.5 mL/min elution with a 5 min linear gradient of acetonitrile/0.1% aq TFA (10/90 through 90/10, v/v), followed by isocratic elution with acetonitrile/0.1% aq TFA (90/10, v/v) for 2 min]
¹H NMR (400 MHz, CDCl₃, as free base) δ 1.38 (br, 2H), 1.73-1.91 (m, 2H), 1.96-2.03 (m, 1H), 2.17-2.26 (m, 1H), 2.34 (dd, J=9.7, 10.1 Hz, 1H), 2.51-2.61 (m, 2H), 2.66-2.73 (m, 2H), 2.99-3.04 (m, 1H), 3.20-3.26 (m, 1H), 3.32-3.48 (m, 2H), 7.09-7.12 (m, 2H), 7.17-7.36 (m, 8H)
mass spectrum (m/e): 311 (M+1)

Example 18

(2S,3R)-3-Amino-1-([2S]-2-methyoxymethyl-pyrrolidin-1-yl)-4-phenyl-butan-2-ol Dihydrochloride

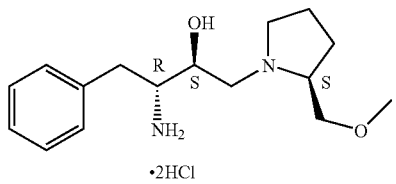

•2HCl

Step A:

[(1R,2S)-1-Benzyl-2-hydroxy-3-([2S]-2-methoxymethyl-pyrrolidin-1-yl)-propyl]-carbamic acid tert-butyl ester Using general procedure 1 and purification method D with [(1R)-1-{(2R)-oxiran-2-yl}-2-phenyl-ethyl]carbamic acid tert-butylester (0.10 g, 0.38 mmol) and (2S)-2-methoxymethyl-pyrrolidine (0.087 g, 0.76 mmol) gives the title compound.
¹H NMR
mass spectrum (m/e): 379 (M+1), 323 (M-C4H8+1)
Step B:

(2S,3R)-3-Amino-1-([2S]-2-methyoxymethyl-pyrrolidin-1-yl)-4-phenyl-butan-2-ol Dihydrochloride Using general procedure 9 and purification method D with [(1R,2S)-1-benzyl-2-hydroxy-3-([2S]-2-methoxymethyl-pyrrolidin-1-yl)-propyl]-carbamic acid tert-butyl ester (0.13 g, 0.34 mmol) gives the title compound.
¹H NMR (400 MHz, CDCl₃, as free base) δ 1.41 (br, 2H), 1.58-1.64 (m, 1H), 1.73-1.80 (m, 2H), 1.88-1.95 (m, 1H), 2.23-2.29 (m, 1H), 2.52 (dd, J=9.6, 13.6 Hz, 1H), 2.59 (dd, J=2.9, 12.1 Hz, 1H), 2.77-2.83 (m, 1H), 2.94-3.01 (m, 2H), 3.09-3.20 (m, 2H), 3.29 (dd, J=5.7, 9.2 Hz, 1H), 3.35 (s, 3H), 3.38 (dd, J=5.3, 8.7 Hz, 1H), 3.53-3.58 (m, 1H), 7.19-7.26 (m, 3H), 7.28-7.32 (m, 2H)
mass spectrum (m/e): 279 (M+1)

Example 19

(2S,3R)-3-Amino-1-([2S]-2-hydroxymethyl-pyrrolidin-1-yl)-4-phenyl-butan-2-ol Dihydrochloride

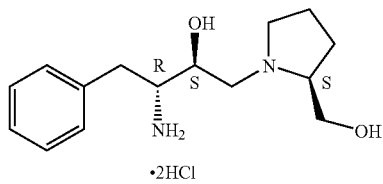

•2HCl

Step A:

[(1R,2S)-1-Benzyl-2-hydroxy-3-([2S]-2-hydroxymethyl-pyrrolidin-1-yl)-propyl]-carbamic acid tert-butyl ester Using general procedure 1 and purification method D with [(1R)-1-{(2R)-oxiran-2-yl}-2-phenyl-ethyl]carbamic acid tert-butylester (0.10 g, 0.38 mmol) and (2S)-2-hydroxymethyl-pyrrolidine (0.077 g, 0.76 mmol) gives the title compound.
¹HNMR
mass spectrum (m/e): 365 (M+1), 309 (M-C4H8+1)
Step B:

(2S,3R)-3-Amino-1-([2S]-2-hydroxymethyl-pyrrolidin-1-yl)-4-phenyl-butan-2-ol Dihydrochloride Using general procedure 9 and purification method D with [(1R,2S)-1-benzyl-2-hydroxy-3-([2S]-2-hydroxymethyl-pyrrolidin-1-yl)-propyl]-carbamic acid tert-butyl ester (0.135 g, 0.38 mmol) gives the title compound.
¹H NMR (400 MHz, CDCl₃, as free base) δ 1.61-1.80 (m, 3H), 1.82-1.92 (m, 1H), 2.27 (br, 2H), 2.24-2.32 (m, 1H, overlapping with H2O peak), 2.49 (dd, J=10.1, 13.6 Hz, 1H), 2.52 (dd, J=2.9, 12.6 Hz, 1H), 2.71-2.76 (m, 1H), 2.91 (dd, J=3.9, 13.1 Hz, 1H), 3.01 (dd, J=10.1, 12.3 Hz, 1H), 3.45 (s, 1H), 3.12-3.23 (m, 2H), 3.49 (dd, J=5.3, 11.9 Hz, 1H), 3.61-3.67 (m, 2H), 7.19-7.26 (m, 3H), 7.28-7.32 (m, 2H)
mass spectrum (m/e): 265 (M+1)

Example 20

(2S,3R)-3-Amino-1-methylamino-4-phenyl-butan-2-ol Dihydrochloride

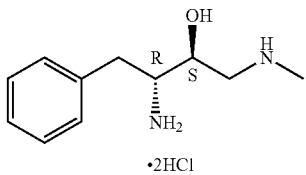

Step A:

[(1R,2S)-1-Benzyl-2-hydroxy-3-methylamino-propyl]-carbamic acid tert-butyl ester Using general procedure 1 with [(1R)-1-{(2R)-oxiran-2-yl}-2-phenyl-ethyl]carbamic acid tert-butylester (0.50 g, 1.9 mmol) and methylamine (10 mL, 8 M solution in ethanol, mmol; used as solvent) gives the title compound.
$^1$H NMR
mass spectrum (m/e): 295 (M+1), 239 (M-C4H8+1), 195 (M-C5H8O2+1)

Step B:

(2S,3R)-3-Amino-1-methylamino-4-phenyl-butan-2-ol Dihydrochloride

Using general procedure 9 with [(1R,2S)-1-benzyl-2-hydroxy-3-methylamino-propyl]-carbamic acid tert-butyl ester (0.106 g, 0.36 mmol) gives the title compound.
$^1$H NMR (400 MHz, CDCl$_3$, as free base) δ 2.28 (br, 3H), 2.48 (dd, J=10.1, 13.6 Hz, 1H), 2.57 (s, 3H), 2.87 (dd, J=8.1, 12.1 Hz, 1H), 2.93-3.02 (m, 2H), 3.15-3.21 (m, 1H), 3.75-3.80 (m, 1H), 7.19-7.30 (m, 3H), 7.29-7.33 (m, 2H)
mass spectrum (m/e): 195 (M+1)

Example 21

N-[(2S,3R)-3-Amino-2-hydroxy-4-phenyl-butyl]-N-methyl-methanesulfonamide Hydrochloride

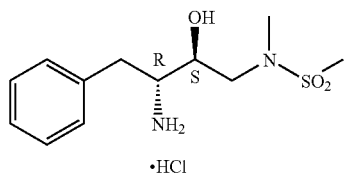

Step A:

[(1R,2S)-1-Benzyl-2-hydroxy-3-(methanesulfonyl-methylamino)-propyl]-carbamic acid tert-butyl ester Using general procedure 5 and purification method D with (2S,3R)-3-amino-1-methylamino-4-phenyl-butan-2-ol (0.10 g, 0.38 mmol) and methane sulfonyl chloride (0.026 mL, 0.34 mmol) gives the title compound.
$^1$H NMR Step B:

N-[(2S,3R)-3-Amino-2-hydroxy-4-phenyl-butyl]-N-methyl-methanesulfonamide Hydrochloride Using general procedure 9 and purification method D with [(1R,2S)-1-benzyl-2-hydroxy-3-(methanesulfonyl-methylamino)-propyl]-carbamic acid tert-butyl ester (0.10 g, 0.30 mmol) gives the title compound.
$^1$H NMR (400 MHz, CDCl$_3$, as free base) δ 1.98 (br, 2H), 2.52 (dd, J=10.1, 13.6 Hz, 1H), 2.86 (s, 3H), 2.95 (s, 3H), 2.94-2.98 (m, 1H, partially overlapping with singlet at 2.95), 3.13-3.17 (m, 1H), 3.29-3.40 (m, 2H), 3.76-3.81 (m, 1H), 7.19-7.26 (m, 3H), 7.29-7.33 (m, 2H)
mass spectrum (m/e): 273 (M+1), 295 (M+Na)

Example 22

N-[(2S,3R)-3-Amino-2-hydroxy-4-phenyl-butyl]-N-methyl-benzamide Hydrochloride

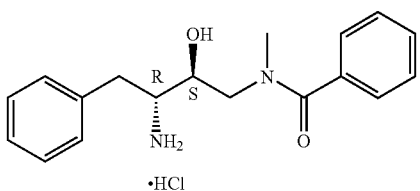

Step A:

[(1R,2S)-3-(Benzoyl-methyl-amino)-1-benzyl-2-hydroxy-propyl]-carbamic acid tert-butyl ester Using general procedure 5 and purification method D with (2S,3R)-3-amino-1-methylamino-4-phenyl-butan-2-ol (0.01 g, 0.38 mmol) and benzoyl chloride (0.039 mL, 0.34 mmol) gives the title compound.
$^1$H NMR Step B:

N-[(2S,3R)-3-Amino-2-hydroxy-4-phenyl-butyl]-N-methyl-benzamide Hydrochloride Using general procedure 9 and purification method D with [(1R,2S)-3-(benzoyl-methyl-amino)-1-benzyl-2-hydroxy-propyl]-carbamic acid tert-butyl ester (0.127 g, 0.36 mmol) gives the title compound.
$^1$H NMR (400 MHz, CDCl$_3$, as free base) δ 2.53-2.59 (m, 1H), 3.06 (s, 3H), 3.06-3.13 (m, 2H, partially overlaps with singlet at 3.06), 3.64 (d, J=13.2 Hz, 1H), 3.83-3.92 (m, 2H), 7.22-7.24 (m, 3H), 7.29-7.33 (m, 2H), 7.40-7.46 (m, 5H)
mass spectrum (m/e): 299 (M+1), 321 (M+Na)

Example 23

N-[(2S,3R)-3-Amino-2-hydroxy-4-phenyl-butyl]-N-methyl-acetamide Hydrochloride

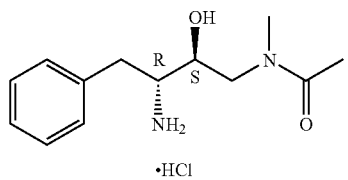

·HCl

Step A:

[(1R,2S)-3-(Acetyl-methyl-amino)-1-benzyl-2-hydroxy-propyl]-carbamic acid tert-butyl ester Using general procedure 5 and purification method D with (2S,3R)-3-amino-1-methylamino-4-phenyl-butan-2-ol (0.10 g, 0.38 mmol) and acetyl chloride (0.019 mL, 0.34 mmol) gives the title compound.
¹HNMR Step B:

N-[(2S,3R)-3-Amino-2-hydroxy-4-phenyl-butyl]-N-methyl-acetamide Hydrochloride

Using general procedure 9 and purification method D with [(1R,2S)-3-(acetyl-methyl-amino)-1-benzyl-2-hydroxy-propyl]-carbamic acid tert-butyl ester (0.72 g, 0.24 mmol) gives the title compound.
¹H NMR (400 MHz, CDCl₃, as free base, major rotamer of approximately 5:1 ratio) δ 2.12 (s, 3H), 2.48-2.56 (m, 1H), 3.01-3.06 (m, 2H), 3.10 (s, 3H), 3.49 (dd, J=1.7, 13.4 Hz, 1H), 3.66-3.75 (m, 2H), 7.20-7.25 (m, 3H), 7.28-7.32 (m, 2H)
mass spectrum (m/e): 237 (M+1), 259 (M+Na)

Example 24

(S)-1-([2S,3R]-3-Amino-2-hydroxy-4-phenyl-butyl)-pyrrolidine-2-carboxylic acid tert-butylamide Dihydrochloride

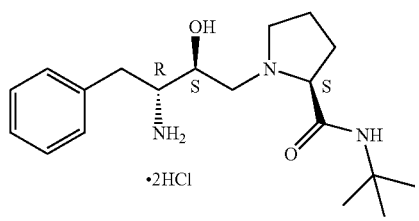

·2HCl

Step A:

[(1R,2S)-1-Benzyl-3-([2S]-2-tert-butylcarbamoyl-pyrrolidin-1-yl)-2-hydroxy-propyl]-carbamic acid tert-butyl ester Using general procedure 1 and purification method D with [(1R)-1-{(2R)-oxiran-2-yl}-2-phenyl-ethyl]carbamic acid tert-butylester (0.21 g, 0.80 mmol) and (S)-proline tert-butyl amide (0.15 g, 0.88 mmol) gives the title compound.
¹H NMR
mass spectrum (m/e): 434 (M+1), 456 (M+Na), 378 (M-C4H8+1), 334 (M-C5H8O2+1)

Step B:

(S)-1-([2S,3R]-3-Amino-2-hydroxy-4-phenyl-butyl)-pyrrolidine-2-carboxylic acid tert-butylamide Dihydrochloride Using general procedure 9 with [(1R,2S)-1-benzyl-3-([2S]-2-tert-butylcarbamoyl-pyrrolidin-1-yl)-2-hydroxy-propyl]-carbamic acid tert-butyl ester (0.25 g, 0.58 mmol) gives the title compound.
¹H NMR (400 MHz, CDCl₃, as free base) δ 1.37 (s, 9H), 1.79-1.84 (m, 3H), 2.13-2.21 (m, 1H), 2.29-2.35 (m, 1H), 2.56-2.63 (m, 2H), 2.80-2.88 (m, 2H), 3.04 (dd, J=6.1, 8.8 Hz, 1H), 3.21-3.26 (m, 1H), 3.34-3.39 (m, 1H), 3.49 (s, 1H), 3.75-3.80 (m, 1H), 7.03 (br, 1H), 7.21-7.26 (m, 3H), 7.30-7.34 (m, 2H)
mass spectrum (m/e): 334 (M+1)

Example 25

(2S,3R)-3-Amino-1-(methyl-phenethylamino)-4-phenyl-butan-2-ol Dihydrochloride

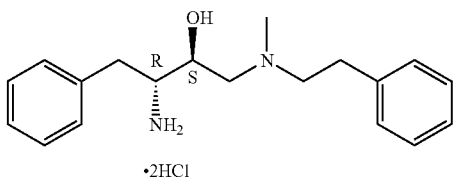

·2HCl

Step A:

[(1R,2S)-1-Benzyl-2-hydroxy-3-(methyl-phenethyl-amino)-propyl]-carbamic acid tert-butyl ester Using general procedure 1 with [(1R)-1-{(2R)-oxiran-2-yl}-2-phenyl-ethyl]carbamic acid tert-butylester (0.30 g, 1.14 mmol) and N-methyl-phenethylamine (0.166 mL, 1.14 mmol) gives the title compound.
¹HNMR
mass spectrum (m/e): 399 (M+1), 343 (M-C4H8+1), 299 (M-C5H8O2+1)

Step B:

(2S,3R)-3-Amino-1-(methyl-phenethylamino)-4-phenyl-butan-2-ol Dihydrochloride

Using general procedure 9 and purification method D with [(1R,2S)-1-benzyl-2-hydroxy-3-(methyl-phenethyl-amino)-propyl]-carbamic acid tert-butyl ester (0.267 g, 0.67 mmol) gives the title compound.
¹H NMR (400 MHz, CDCl₃, as free base) δ 1.62 (br, 2H), 2.38 (s, 3H), 2.49 (d, J=9.7, 13.6 Hz, 1H), 2.53 (d, J=3.1, 11.9 Hz, 1H), 2.64-2.75 (m, 2H), 2.78-2.83 (m, 3H), 2.93 (dd, J=4.0, 13.2 Hz, 1H), 2.97-3.15 (m, 1H), 3.49 (s, 1H), 3.55-3.60 (m, 1H), 7.18-7.33 (m, 10H)
mass spectrum (m/e): 299 (M+1)

Example 26

(2S,3R)-3-Amino-1-phenethylamino-4-phenyl-butan-2-ol Dihydrochloride

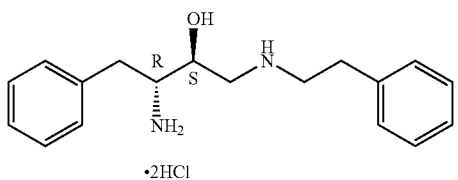

Step A:

[(1R,2S)-1-Benzyl-2-hydroxy-3-phenethyl-amino-propyl]-carbamic acid tert-butyl ester Using general procedure 1 and purification method D with [(1R)-1-{(2R)-oxiran-2-yl}-2-phenyl-ethyl]carbamic acid tert-butylester (0.263 g, 1.0 mmol) and phenethylamine (0.126 g, 1.0 mmol) gives the title compound.

¹HNMR mass spectrum (m/e): 385 (M+1), 329 (M-C4H8+1), 285 (M-C5H8O2+1)

Step B:

(2S,3R)-3-Amino-1-phenethylamino-4-phenyl-butan-2-ol Dihydrochloride

Using general procedure 9 and purification method D with [(1R,2S)-1-benzyl-2-hydroxy-3-phenethyl-amino-propyl]-carbamic acid tert-butyl ester (0.105 g, 0.28 mmol) gives the title compound.

¹H NMR (400 MHz, CDCl₃, as free base) δ 1.96 (br, 3H), 2.47 (d, J=10.1, 13.6 Hz, 1H), 2.76 (d, J=8.8, 12.1 Hz, 1H), 2.82-2.99 (m, 6H), 3.10-3.15 (m, 1H), 3.49 (s, 1H), 3.56-3.60 (m, 1H), 7.18-7.25 (m, 6H), 7.28-7.33 (m, 4H)

mass spectrum (m/e): 285 (M+1)

Example 27

(2S,3R)-3-Amino-1-benzylamino-4-phenyl-butan-2-ol Dihydrochloride

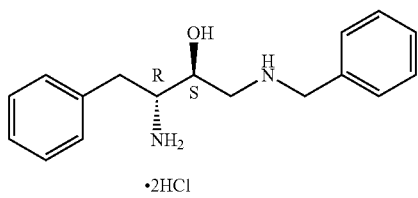

Step A:

[(1R,2S)-1-Benzyl-3-benzylamino-2-hydroxy-propyl]-carbamic acid tert-butyl ester Using general procedure 1 and purification method D with [(1R)-1-{(2R)-oxiran-2-yl}-2-phenyl-ethyl]carbamic acid tert-butylester (0.263 g, 1.0 mmol) and benzylamine (0.11 mL, 1.0 mmol) gives the title compound.

¹H NMR mass spectrum (m/e): 371 (M+1), 315 (M-C4H8+1), 271 (M-C5H8O2+1), 393 (M+Na)

Step B:

(2S,3R)-3-Amino-1-benzylamino-4-phenyl-butan-2-ol Dihydrochloride

Using general procedure 9 with [(1R,2S)-1-benzyl-3-benzylamino-2-hydroxy-propyl]-carbamic acid tert-butyl ester (0.23 g, 0.62 mmol) gives the title compound.

¹H NMR (400 MHz, CDCl₃, as free base) δ 2.53 (br, 2H), 2.43 (dd, J=9.7, 13.6 Hz, 1H), 2.80-2.89 (m, 2H), 2.97 (dd, J=3.5, 11.9 Hz, 1H), 3.16-3.21 (m, 1H), 3.49 (s, 1H), 3.65-3.70 (m, 1H), 3.83 (d, J=13.2 Hz, 1H), 3.93 (d, J=13.2 Hz, 1H), 7.16 (d, J=7.2 Hz, 2H), 7.20-7.32 (m, 5H), 7.26-7.37 (m, 3H)

mass spectrum (m/e): 271 (M+1)

Example 28

(2S,3R)-3-Amino-1-dimethylamino-4-phenyl-butan-2-ol Dihydrochloride

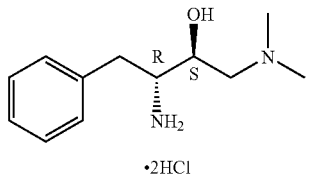

Step A:

[(1R,2S)-1-Benzyl-3-dimethylamino-2-hydroxy-propyl]-carbamic acid tert-butyl ester Using general procedure 1 with [(1R)-1-{(2R)-oxiran-2-yl}-2-phenyl-ethyl]carbamic acid tert-butylester (0.283 g, 1.1 mmol) and dimethylamine (2.7 mL, 2M solution in THF, 5.4 mmol) gives the title compound.

¹H NMR

Step B:

(2S,3R)-3-Amino-1-dimethylamino-4-phenyl-butan-2-ol Dihydrochloride

Using general procedure 9 with [(1R,2S)-1-benzyl-3-dimethylamino-2-hydroxy-propyl]-carbamic acid tert-butyl ester (0.32 g, 1.03 mmol) gives the title compound.

¹H NMR (400 MHz, CDCl₃, as free base) δ 1.62 (br, 2H), 2.34 (s, 6H), 2.42 (dd, J=3.1, 11.8 Hz, 1H), 2.49 (dd, J=9.7, 13.2 Hz, 1H), 2.62 (dd, J=10.5, 12.3 Hz, 1H), 2.96 (dd, J=3.1, 13.2 Hz, 1H), 3.11-3.16 (m, 1H), 3.49 (s, 1H), 3.49 (s, 1H), 3.59-3.64 (m, 1H), 7.20-7.25 (m, 3H), 7.29-7.34 (m, 2H)

mass spectrum (m/e): 209 (M+1)

Example 29

(2S,3R)-3-Amino-1-(benzyl-methylamino)-4-phenyl-butan-2-ol Dihydrochloride

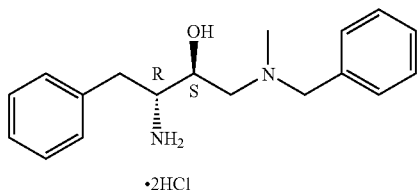

•2HCl

Step A:

[(1R,2S)-1-Benzyl-3-(benzyl-methyl-amino)-2-hydroxy-propyl]-carbamic acid tert-butyl ester Using general procedure 1 and purification method D with [(1R)-1-{(2R)-oxiran-2-yl}-2-phenyl-ethyl]carbamic acid tert-butylester (0.255 g, 0.97 mmol) and N-methyl-benzylamine (0.25 mL, 1.9 mmol) gives the title compound.

$^1$HNMR mass spectrum (m/e): 385 (M+1), 329 (M-C4H8+1), 285 (M-C5H8O2+1), 407 (M+Na)

Step B:

(2S,3R)-3-Amino-1-(benzyl-methylamino)-4-phenyl-butan-2-ol Dihydrochloride

Using general procedure 9 with [(1R,2S)-1-benzyl-3-(benzyl-methyl-amino)-2-hydroxy-propyl]-carbamic acid tert-butyl ester (0.22 g, 0.57 mmol) gives the title compound.

$^1$H NMR (400 MHz, CDCl$_3$, as free base) δ 1.37 (br, 2H), 2.26 (s, 3H), 2.49 (dd, J=9.7, 13.6 Hz, 1H), 2.54 (dd, J=3.5, 12.3 Hz, 1H), 2.70 (dd, J=10.5, 12.3 Hz, 1H), 2.95 (dd, J=3.5, 13.6 Hz, 1H), 3.10-3.16 (m, 1H), 3.48 (s, 1H), 3.51 (d, J=13.1 Hz, 1H), 3.63-3.69 (m, 1H), 3.70 (d, J=13.1 Hz, 1H), 7.19-7.36 (m, 10H)

mass spectrum (m/e): 285 (M+1)

Example 30

(2S,3R)-3-Amino-1-(1,3-dihydro-isoindol-2-yl)-4-phenyl-butan-2-ol Dihydrochloride

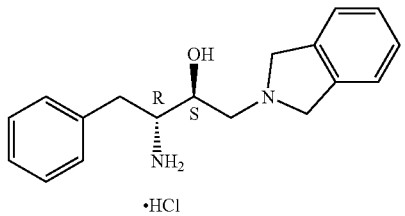

•HCl

Step A:

[(1R,2S)-1-Benzyl-3-(1,3-dihydro-isoindol-2-yl)-2-hydroxy-propyl]-carbamic acid tert-butyl ester Using general procedure 1 with [(1R)-1-{(2R)-oxiran-2-yl}-2-phenyl-ethyl]carbamic acid tert-butylester (0.132 g, 0.50 mmol) and 2,3-dihydro-1H-isoindole (0.114 mL, 1.0 mmol) gives the title compound.

$^1$H NMR mass spectrum (m/e): 383 (M+1), 327 (M-C4H8+1), 283 (M-C5H8O2+1)

Step B:

(2S,3R)-3-Amino-1-(1,3-dihydro-isoindol-2-yl)-4-phenyl-butan-2-ol Dihydrochloride Using general procedure 7 and purification method D with [(1R,2S)-1-benzyl-3-(1,3-dihydro-isoindol-2-yl)-2-hydroxy-propyl]-carbamic acid tert-butyl ester (0.146 g, 0.38 mmol) gives the title compound.

$^1$H NMR (400 MHz, CDCl$_3$, as free base) δ 1.62 (br, 2H), 2.56 (dd, J=10.0, 13.5 Hz, 1H), 2.88 (dd, J=3.1, 11.9 Hz, 1H), 2.97-3.05 (m, 2H), 3.19-3.24 (m, 1H), 3.68-3.73 (m, 1H), 3.95 (d, J=11.0 Hz, 2H), 4.12 (d, J=11.0 Hz, 2H), 7.17-7.26 (m, 7H), 7.30-7.34 (m, 2H)

mass spectrum (m/e): 283 (M+1)

Example 31

(2S,3R)-3-Amino-4-phenyl-1-(3-trifluoromethyl-5,6-dihydro-8H-[1,2,4]triazolo[4,3-a]pyrazin-7-yl)-butan-2-ol Hydrochloride

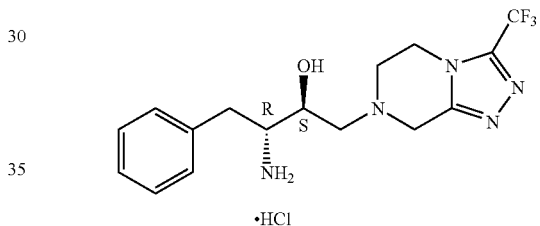

•HCl

Step A:

[(1R,2S)-1-Benzyl-2-hydroxy-3-(3-trifluoromethyl-5,6-dihydro-8H-[1,2,4]triazolo[4,3a]pyrazin-7-yl)-propyl]-carbamic acid tert-butyl ester Using general procedure 1 and purification method D with [(1R)-1-{(2R)-oxiran-2-yl}-2-phenyl-ethyl]carbamic acid tert-butylester (0.132 g, 0.50 mmol) and 3-trifluoromethyl-5,6,7,8-tetrahydro-[1,2,4]triazolo[4,3-a]pyrazine (0.096 g, 0.50 mmol) gives the title compound.

$^1$H NMR mass spectrum (m/e): 456 (M+1), 400 (M-C4H8+1), 356 (M-C5H8O2+1), 478 (M+Na)

Step B:

(2S,3R)-3-Amino-4-phenyl-1-(3-trifluoromethyl-5,6-dihydro-8H-[1,2,4]triazolo[4,3-a]pyrazin-7-yl)-butan-2-ol Hydrochloride Using general procedure 7 with [(1R,2S)-1-benzyl-2-hydroxy-3-(3-trifluoromethyl-5,6-dihydro-8H-[1,2,4]triazolo[4,3a]pyrazin-7-yl)-propyl]-carbamic acid tert-butyl ester (0.146 g, 0.38 mmol) gives the title compound.

$^1$H NMR (400 MHz, CDCl$_3$ with drop of D$_5$-pyridine) δ 2.57 (dd, J=7.0, 13.2 Hz, 1H), 2.65-2.75 (m, 2H), 2.92-2.95 (m, 1H), 3.09-3.21 (m, 2H), 3.77 (d, J=15.6 Hz, 1H), 3.91-4.09 (m, 4H), 4.41-4.48 (m, 1H), 7.14-7.28 (m, 5H)

mass spectrum (m/e): 356 (M+1), 378 (M+Na)

Example 32

(2S,3R)-3-Amino-1-(3,4-dihydro-1H-isoquinolin-2-yl)-4-phenyl-butan-2-ol Dihydrochloride

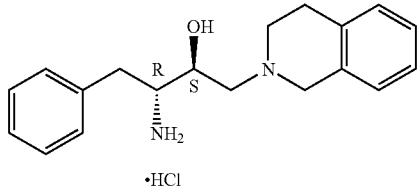

·HCl

Step A:

[(1R,2S)-1-Benzyl-3-(3,4-dihydro-1H-isoquinolin-2-yl)-2-hydroxy-propyl]-carbamic acid tert-butyl ester Using general procedure 1 with [(1R)-1-{(2R)-oxiran-2-yl}-2-phenyl-ethyl]carbamic acid tert-butylester (0.132 g, 0.50 mmol) and 1,2,3,4-tetrahydro-isoquinoline (0.127 mL, 1.0 mmol) gives the title compound.
$^1$H NMR
mass spectrum (m/e): 397 (M+1), 341 (M-C4H8+1), 297 (M-C5H8O2+1)

Step B:

(2S,3R)-3-Amino-1-(3,4-dihydro-1H-isoquinolin-2-yl)-4-phenyl-butan-2-ol Dihydrochloride Using general procedure 7 and purification method A with [(1R,2S)-1-benzyl-3-(3,4-dihydro-1H-isoquinolin-2-yl)-2-hydroxy-propyl]-carbamic acid tert-butyl ester (0.115 g, 0.29 mmol) gives the title compound.
$^1$H NMR (400 MHz, CDCl$_3$, as free base) δ 1.73 (br, 2H), 2.58 (dd, J=9.7, 13.7 Hz, 1H), 2.72 (dd, J=3.5, 11.7 Hz, 1H), 2.78-2.81 (m, 2H), 2.95-3.03 (m, 4H), 3.21-3.25 (m, 1H), 3.67 (d, J=15.0 Hz, 1H), 3.78-3.82 (m, 1H), 3.87 (d, J=15.0 Hz, 1H), 7.01-7.04 (m, 1H), 7.11-7.17 (m, 3H), 7.21-7.26 (m, 3H), 7.30-7.34 (m, 2H)
mass spectrum (m/e): 297 (M+1)

Example 33

(2S,3R)-3-Amino-4-phenyl-1-piperidin-1-yl-butan-2-ol Dihydrochloride

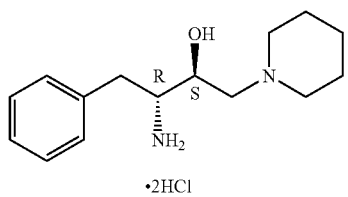

·2HCl

Step A:

[(1R,2S)-1-Benzyl-2-hydroxy-3-piperidin-1-yl-propyl]-carbamic acid tert-butyl ester Using general procedure 1 with [(1R)-1-{(2R)-oxiran-2-yl}-2-phenyl-ethyl]carbamic acid tert-butylester (0.115 g, 0.44 mmol) and piperidine (0.218 mL, 2.20 mmol) give the title compound.

$^1$H NMR
mass spectrum (m/e): 349 (M+1), 293 (M-C4H8+1), 249 (M-C5H8O2+1)

Step B:

(2S,3R)-3-Amino-4-phenyl-1-piperidin-1-yl-butan-2-ol Dihydrochloride

Using general procedure 7 and purification method B with [(1R,2S)-1-benzyl-2-hydroxy-3-piperidin-1-yl-propyl]-carbamic acid tert-butyl ester (0.106 g, 0.31 mmol) gives the title compound.
$^1$H NMR (400 MHz, DMSO-d$_6$) δ 1.60-1.73 (m, 1H), 1.73-1.84 (m, 4H), 2.81-2.99 (m, 4H), 3.03-3.07 (m, 1H), 3.25-3.54 (m, 4H), 4.06 (br, 1H), 4.27 (br d, 1H), 6.25 (br, 1H), 7.25-7.27 (m, 1H), 7.31-7.38 (m, 4H), 8.16 (br, 3H), 10.05, (br, 1H)
mass spectrum (m/e): 249 (M+1)

Example 34

(2S,3R)-3-Amino-4-phenyl-1-pyrrolidin-1-yl-butan-2-ol Dihydrochloride

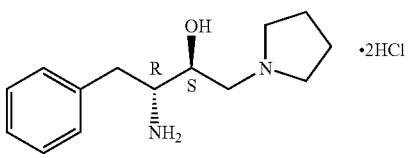

·2HCl

Step A:

[(1R,2S)-1-Benzyl-2-hydroxy-3-pyrrolidin-1-yl-propyl]-carbamic acid tert-butyl ester Using general procedure 1 with [(1R)-1-{(2R)-oxiran-2-yl}-2-phenyl-ethyl]carbamic acid tert-butylester (0.133 g, 0.50 mmol) and pyrrolidine (0.210 mL, 2.50 mmol) gives the title compound.
$^1$HNMR
mass spectrum (m/e): 335 (M+1), 291 (M-C4H8+1), 235 (M-C5H8O2+1)

Step B:

(2S,3R)-3-Amino-4-phenyl-1-pyrrolidin-1-yl-butan-2-ol Dihydrochloride

Using general procedure 7 and purification method B with [(1R,2S)-1-benzyl-2-hydroxy-3-pyrrolidin-1-yl-propyl]-carbamic acid tert-butyl ester (0.121 g, 0.36 mmol) gives the title compound.
$^1$H NMR (400 MHz, DMSO-d$_6$) δ 1.84-1.93 (m, 2H), 1.94-2.04 (m, 2H), 2.83 (dd, J=8.4, 14.5 Hz, 1H), 2.88-3.08 (m, 3H), 3.21-3.35 (m, 1H), 3.40-3.60 (m, 4H, obscured by H2O peak), 4.15 (br d, J=9.7 Hz, 1H), 6.29 (br, 1H), 7.24-7.29 (m, 1H), 7.31-7.35 (m, 4H), 8.15 (br, 3H), 10.25 (br, 1H)
mass spectrum (m/e): 235 (M+1)

Example 35

(2S,3R)-3-Amino-1-morpholin-4-yl-4-phenyl-butan-2-ol Dihydrochloride

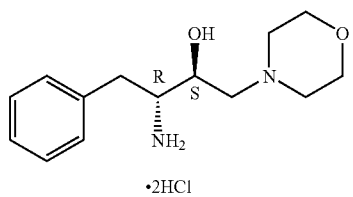

•2HCl

Step A:

[(1R,2S)-1-Benzyl-2-hydroxy-3-morpholin-4-yl-propyl]-carbamic acid tert-butyl ester Using general procedure 1 with [(1R)-1-{(2R)-oxiran-2-yl}-2-phenyl-ethyl]carbamic acid tert-butylester (0.133 g, 0.50 mmol) and morpholine (0.220 mL, 2.50 mmol) gives the title compound.
$^1$HNMR
mass spectrum (m/e): 351 (M+1), 295 (M-C4H8+1), 251 (M-C5H8O2+1)

Step B:

(2S,3R)-3-Amino-1-morpholin-4-yl-4-phenyl-butan-2-ol Dihydrochloride

Using general procedure 7 and purification method B with [(1R,2S)-1-benzyl-2-hydroxy-3-morpholin-4-yl-propyl]-carbamic acid tert-butyl ester (0.139 g, 0.400 mmol) gives the title compound.
$^1$HNMR: (400 mHz, MeOD) δ 2.84 (dd, J=8.1, 14.5 Hz, 1H), 2.92 (dd, J=5.7, 14.5 Hz, 1H), 3.02-3.23 (m, 3H), 3.35-3.64 (m, 4H, obscured by H2O peak), 3.74-3.99 (m, 4H), 4.33 (br d, J=8.3 Hz, 1H), 6.33 (br, 1H), 7.23-7.30 (m, 1H), 7.32-7.38 (m, 4H), 8.20 (br, 3H), 10.21 (br, 1H)
mass spectrum (m/e): 251 (M+1)

Example 36

(S)-1-([2S,3R]-3-Amino-2-hydroxy-4-[2,5-difluoro-phenyl]-butyl)-pyrrolidine-2-carboxylic acid tert-butylamide Dihydrochloride

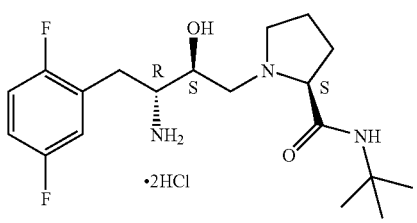

Step A:

[(1R,2S)-1-(2,5-Difluoro-benzyl)-3-([2S]-2-tert-butylcarbamoyl-pyrrolidin-1-yl)-2-hydroxy-propyl]-carbamic acid tert-butyl ester Using general procedure 1 and purification method D with [(1R)-1-{(2R)-oxiran-2-yl}-2-(2,5-difluoro-phenyl)-ethyl] carbamic acid tert-butylester (0.213 g, 0.71 mmol) and (S)-proline tert-butyl amide (0.133 g, 0.78 mmol) gives the title compound.
$^1$H NMR
mass spectrum (m/e): 470 (M+1), 414 (M-C4H8+1), 370 (M-C5H8O2+1), 492 (M+Na)

Step B:

(S)-1-([2S,3R]-3-Amino-2-hydroxy-4-[2,5-difluoro-phenyl]-butyl)-pyrrolidine-2-carboxylic acid tert-butylamide Dihydrochloride Using general procedure 7 and purification method D with [(1R,2S)-1-(2,5-difluoro-benzyl)-3-([2S]-2-tert-butylcarbamoyl-pyrrolidin-1-yl)-2-hydroxy-propyl]-carbamic acid tert-butyl ester (0.227 g, 0.48 mmol) gives the title compound.
$^1$H NMR (400 MHz, CH$_3$OD, as free base) δ 1.32 (s, 9H), 1.71-1.80 (m, 3H), 2.09-2.16 (m, 1H), 2.26-2.32 (m, 1H), 2.54-2.67 (m, 3H), 2.87-2.95 (m, 2H), 2.98-3.04 (m, 1H), 3.20-3.26 (m, 1H), 3.61-3.65 (m, 1H), 6.92-6.97 (m, 1H), 7.02-7.08 (m, 2H)
mass spectrum (m/e): 370 (M+1)

Example 37

(2S,3R)-3-Amino-4-(2,5-difluoro-phenyl)-1-pyrrolidin-1-yl-butan-2-ol Dihydrochloride

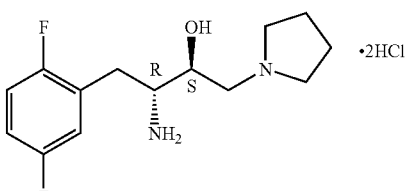

Step A:

[(1R,2S)-1-(2,4-Difluoro-benzyl)-2-hydroxy-3-pyrrolidin-1-yl-propyl]-carbamic acid tert-butyl ester Using general procedure 1 and purification method D with [(1R)-1-{(2R)-oxiran-2-yl}-2-(2,5-difluoro-phenyl)-ethyl] carbamic acid tert-butylester (0.40 g, 1.3 mmol) and pyrrolidine (0.553 mL, 6.70 mmol) gives the title compound.
$^1$H NMR
mass spectrum (m/e): 371 (M+1), 315 (M-C4H8+1), 393 (M+Na)

Step B:

(2S,3R)-3-Amino-4-(2,5-difluoro-phenyl)-1-pyrrolidin-1-yl-butan-2-ol Dihydrochloride Using general procedure 7 and purification method D with [(1R,2S)-1-(2,4-difluoro-benzyl)-2-hydroxy-3-pyrrolidin-1-yl-propyl]-carbamic acid tert-butyl ester (0.406 g, 1.1 mmol) gives the title compound.
$^1$H NMR (400 MHz, CH$_3$OD, as free base) δ 1.75-1.81 (m, 4H), 2.52-2.65 (m, 7H), 2.93 (dd, J=3.3, 13.8 Hz, 1H), 2.98-3.03 (m, 1H), 3.63-3.67 (m, 1H), 6.92-6.97 (m, 1H), 7.02-7.08 (m, 2H)
mass spectrum (m/e): 271 (M+1)

Example 38

(2S,3R)-3-Amino-1-(3,4-dihydro-1H-isoquinolin-2-yl)-4-(2,5-difluoro-phenyl)-butan-2-ol Dihydrochloride

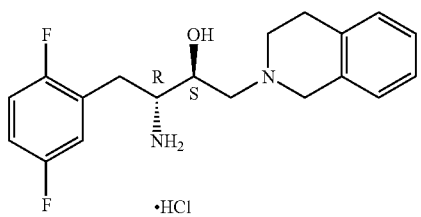

Step A:

[(1R,2S)-1-(2,5-Difluoro-benzyl)-3-(3,4-dihydro-1H-isoquinolin-2-yl)-2-hydroxy-propyl]-carbamic acid tert-butyl ester Using general procedure 1 and purification method D with [(1R)-1-{(2R)-oxiran-2-yl}-2-(2,5-difluoro-phenyl)-ethyl] carbamic acid tert-butylester (0.385 g, 1.3 mmol) and 1,2,3,4,-tetrahydro-isoquinoline (0.200 mL, 1.50 mmol) gives the title compound.
$^1$HNMR
mass spectrum (m/e): 433 (M+1), 377 (M-C4H8+1), 455 (M+Na)

Step B:

(2S,3R)-3-Amino-1-(3,4-dihydro-1H-isoquinolin-2-yl)-4-(2,5-difluoro-phenyl)-butan-2-ol Dihydrochloride Using general procedure 7 and purification method D with [(1R,2S)-1-(2,5-difluoro-benzyl)-3-(3,4-dihydro-1H-isoquinolin-2-yl)-2-hydroxy-propyl]-carbamic acid tert-butyl ester (0.407 g, 0.94 mmol) gives the title compound.
$^1$H NMR (400 MHz, CH$_3$OD, as free base) δ 2.58-2.73 (m, 3H), 2.80-2.84 (m, 2H), 2.86-2.90 (m, 2H), 3.01 (dd, J=3.7, 13.4 Hz, 1H), 3.10-3.15 (m, 1H), 3.66 (d, J=14.7 Hz, 1H), 3.72 (d, J=14.7 Hz, 1H), 3.79-3.83 (m, 1H), 6.92-7.09 (m, 7H)
mass spectrum (m/e): 333 (M+1)

Example 39

N-[(2S,3R)-3-Amino-2-hydroxy-4-(2,5-difluoro-phenyl)-butyl]-N-methyl-acetamide Hydrochloride

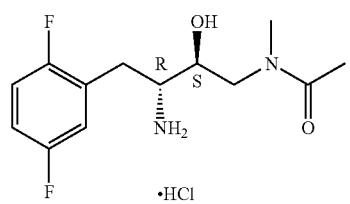

Step A:

[(1R,2S)-1-(2,5-Difluoro-benzyl)-2-hydroxy-3-methylamino-propyl]-carbamic acid tert-butyl ester Using general procedure 1 and purification method D with [(1R)-1-{(2R)-oxiran-2-yl}-2-(2,5-difluoro-phenyl)-ethyl] carbamic acid tert-butylester (0.17 g, 0.57 mmol) and methylamine (7 mL, 2M solution in methanol, 14 mmol; used as solvent) gives the title compound.
$^1$H NMR Step B:

[(1R,2S)-3-(Acetyl-methyl-amino)-1-(2,5-difluoro-benzyl)-2-hydroxy-propyl]-carbamic acid tert-butyl ester Using general procedure 5 with [(1R,2S)-1-(2,5-difluoro-benzyl)-2-hydroxy-3-methylamino-propyl]-carbamic acid tert-butyl ester (0.107 g, 0.32 mmol) and acetyl chloride (0.020 mL, 0.32 mmol) gives the title compound.
$^1$H NMR
mass spectrum (m/e): 373 (M+1), 317 (M-C4H8+1), 273 (M-C5H8O2+1), 395 (M+Na)

Step C:

N-[(2S,3R)-3-Amino-2-hydroxy-4-(2,5-difluoro-phenyl)-butyl]-N-methyl-acetamide Hydrochloride Using general procedure 9 and purification method D with [(1R,2S)-3-(acetyl-methyl-amino)-1-(2,5-difluoro-benzyl)-2-hydroxy-propyl]-carbamic acid tert-butyl ester (0.105 g, 0.28 mmol) gives the title compound.
$^1$H NMR (400 MHz, CH$_3$OD, as free base, approximately 3:2 ratio of rotamers) δ 2.09 and 2.12 (s, 3H), 2.34-2.62 (m, 1H), 2.91-3.02 (m, 2H), 3.12 and 3.13 (s, 3H), 3.37-3.44 (m, 1H), 3.50-3.63 (m, 1H), 3.65-3.72 (m, 1H), 6.93-6.96 (m, 1H), 7.02-7.10 (m, 2H)
mass spectrum (m/e): 273 (M+1), 295 (M+Na)

The compound of formula I is preferably formulated in a unit dosage form prior to administration. Therefore, yet another aspect of the present invention is a pharmaceutical composition comprising a compound of formula I and one or more pharmaceutically acceptable carriers, diluents or excipients.

The present pharmaceutical compositions are prepared by known procedures using well-known and readily available ingredients. In making the formulations of the present invention, the active ingredient (formula I compound) will usually be mixed with a carrier, or diluted by a carrier, or enclosed within a carrier which may be in the form of a capsule, sachet, paper or other container. When the carrier serves as a diluent, it may be a solid, semisolid or liquid material that acts as a vehicle, excipient, or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions of the present invention may be formulated in sustained release form to provide the rate controlled release of any one or more of the components or active ingredients to optimize the therapeutic effects, i.e., antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration, Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

The pharmacological profile of the present compounds may be demonstrated as follows:

Human Recombinant DPIV Activity Assay

The DPIV assay used was a fluorometric end point assay (excitation 355 nm; emission 460 nm) using enriched human recombinant DPIV enzyme (21.3 µU/µl), and Gly-Pro-AMC (Bachem I-1225) as substrate (0.02 mM). Secreted DPIV (lacking membrane anchor) was enriched from HEK293 cell culture supernatant by ultrafiltration, ultra-centrifugation, and size-exclusion chromatography. IC50 values of the compounds were calculated based on a 12 points concentration response curve. Each concentration was measured as duplicates. The assay was validated by plate variability and conformity, inter-plate variability, signal window, and minimum significant ration of IC50. A MSR was calculated based on a test/retest analysis and a retrospective analysis. The MSR value is 1.8.

Using this assay the preferred compounds of the invention described within the examples show activity with an IC50 less than or equal to 100 µM.

| Example | IC50 (µM) |
|---|---|
| 6 | 2.734 |
| 13 | 2.990 |
| 15 | 4.334 |
| 21 | 9.761 |

We claim:

1. A compound of the formula III:

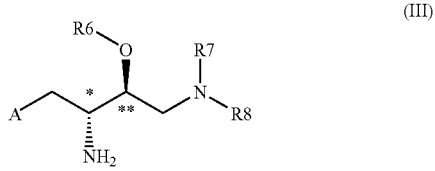

wherein

A is

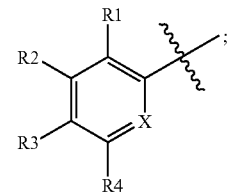

R1 is H or halo;
R2 and R3 are H;
R4 is H or halo;
X is CH;
R6 is H;
R7 is H or $C_1$-$C_6$ alkyl;
R8 is $C_1$-$C_6$ alkyl, $C_1$-$C_6$ alkylaryl, C(O)R9 and —$SO_2$R9, or R7 and R8 combine to form

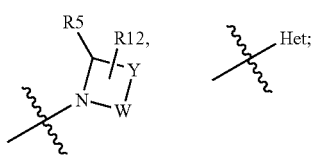

R9 is selected from $C_1$-$C_6$ alkyl, aryl, and $C_1$-$C_6$ alkylaryl,
R5 is H;
Y is selected from —$CH_2$—Y'—, —$CH_2$—$CH_2$—Y'—, —Y'—$CH_2$—, —Y'—$CH_2$—$CH_2$— and —$CH_2$—Y"—$CH_2$—;
Y' is selected from CR11 and CR15;
Y" is selected from CR11, CR15, NR16, and O;
W is CR10;
R10 is selected from H, —C(O)NR13R14, aryl, $C_1$-$C_6$ alkyl-O—$C_1$-$C_6$ alkyl and hydroxy $C_1$-$C_6$ alkyl;
R11 and R12 are independently selected from H $C_1$-$C_6$ alkyl, and aryl;
R13 and R14 are independently selected from H and $C_1$-$C_6$ alkyl;
R15 combines with R11 or R12 to form a phenyl ring;
R16 combines with R11 or R12 to form a 5-6 membered heteroaryl ring optionally substituted with $CF_3$;
where R10, is aryl optionally substituted with F;
Het is a N-linked 5-membered heteroaryl ring optionally substituted with aryl, or a N-linked 5-membered heteroaryl ring fused with phenyl;
with the proviso that a compound of formula III is not 1-(3-Amino-2-hydroxy-4-phenyl-butyl)-pyrrolidine-2-carboxylic acid (2-pyridin-2-yl-ethyl)-amide.

2. A compound according to claim 1 of the formula IIIa:

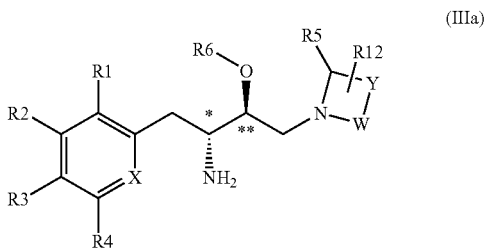

(IIIa)

or a pharmaceutically acceptable salt thereof.

3. A compound according to claim 1 of the formula IIIb:

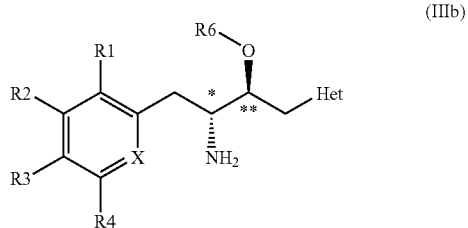

(IIIb)

or a pharmaceutically acceptable salt thereof.

4. A compound according to claim 1 of the formula IIIa(i):

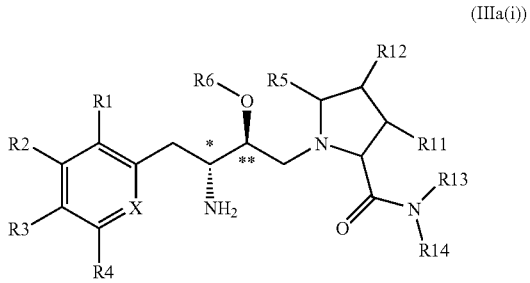

(IIIa(i))

or a pharmaceutically acceptable salt thereof.

5. A compound according to claim 1 wherein R7 is selected from H and $CH_3$.

6. A compound according to claim 1 wherein R8 is selected from $C_1$-$C_4$ alkyl, $C_1$-$C_4$ alkylaryl and —C(O)R9.

7. A compound according to claim 1 wherein R8 is selected from methyl, phenylethyl, phenylpropyl and —C(O)R9.

8. A compound according to claim 1 wherein R9 is selected from methyl, phenylethyl and phenylpropyl.

9. A compound according to claim 1 wherein Y is selected from —Y'—$CH_2$—$CH_2$—, —$CH_2$—Y"—$CH_2$— or —$CH_2$—$CH_2$—Y'— where Y' or Y" is CR15 and R15 combines with R11 or R12 to form a phenyl.

10. A compound according to claim 1 wherein Y is —$CH_2$—Y"—$CH_2$— where Y" is NR16 and R16 combines with R11 or R12 to form a pyrrolyl, imidazolyl or triazolyl substituent optionally substituted with $CF_3$.

11. A compound according to claim 1 wherein Y is —$CH_2$—Y"—$CH_2$— where Y" is NR16 and R16 combines with R11 or R12 to form a 1,2,3-triazolyl or 1,2,4 triazolyl substituent optionally substituted with $1CF_3$ substituent.

12. A compound according to claim 1 wherein Het is selected from a pyrazolyl, imidazolyl or triazolyl substituent.

13. A compound according to claim 1 wherein Het is selected from 1,2,3-triazol-1-yl, 1,2,3-triazol-2-yl and 1,2,4-triazol-1-yl.

14. A compound according to claim 1 wherein Het is selected from a pyrrolyl, pyrazolyl, imidazolyl or triazolyl substituent fused with phenyl.

15. A compound according to claim 1 wherein Het is selected from benzotriazol-1-yl, benzotriazol-2-yl, indazol-1-yl, indazol-2-yl or benzimidazol-1-yl.

16. A compound according to claim 1 wherein R11 is H.

17. A compound according to claim 1 wherein R12 is H.

18. A compound according to claim 1 wherein R13 and R14 are independently selected from H and $C_1$-$C_4$ alkyl.

19. A compound according to claim 1 wherein R13 and R14 are independently selected from H, methyl, isopropyl, and t-butyl.

20. A compound according to a claim 1 wherein R13 is H.

21. A compound according to claim 1 wherein R14 is t-butyl.

22. A compound according to claim 1 wherein R1 and R4 are independently selected from H, F, and Cl.

23. A compound according to claim 1 wherein R1 and R4 are independently selected from F.

24. A compound according to claim 1 wherein R1 is F and R4 is either Cl or F.

25. A pharmaceutical composition comprising a compound of formula III according to claim 1
or a pharmaceutically acceptable salt thereof,
and a pharmaceutically acceptable diluent or carrier.

26. A pharmaceutical composition of claim 25 additionally comprising metformin.

27. A method for the therapeutic treatment of a condition selected from type II diabetes, obesity, hyperglycemia and a lipid disorder, which comprises administering a compound of formula III according to claim 1:
to a human being or animal in need thereof.

* * * * *